United States Patent
Allegrini et al.

(10) Patent No.: US 8,329,937 B2
(45) Date of Patent: Dec. 11, 2012

(54) METHOD FOR PURIFYING 4-(NITROOXY)BUTYL(2S)-2-(6-METHOXY-2-NAPHTHYL) PROPANOATE

(75) Inventors: Pietro Allegrini, Mereto di Tomba (IT); Tiziano Scubla, Mereto di Tomba (IT); Nicoletta Toniutti, Mereto di Tomba (IT); Romano Rivolta, Sophia Antipolis-Valbonne (FR); Thierry Delahaique, Sophia Antipolis-Valbonne (FR)

(73) Assignee: Nicox S.A., Sophia Antipolis-Valbonne (FR)

( * ) Notice: Subject to any disclaimer, the term of this patent is extended or adjusted under 35 U.S.C. 154(b) by 231 days.

(21) Appl. No.: 12/682,249

(22) PCT Filed: Jun. 18, 2009

(86) PCT No.: PCT/IB2009/006382
§ 371 (c)(1),
(2), (4) Date: Jun. 18, 2009

(87) PCT Pub. No.: WO2009/153668
PCT Pub. Date: Dec. 23, 2009

(65) Prior Publication Data
US 2010/0256411 A1 Oct. 7, 2010

(30) Foreign Application Priority Data

Jun. 20, 2008 (IT) .............................. RM2008A0325

(51) Int. Cl.
*C07C 203/04* (2006.01)
(52) U.S. Cl. ....................................................... 558/482
(58) Field of Classification Search .................... 558/482
See application file for complete search history.

(56) References Cited

U.S. PATENT DOCUMENTS
2008/0269323 A1 10/2008 Prasad et al.

FOREIGN PATENT DOCUMENTS
WO WO-01/10814 A1 2/2001
WO WO-2004/012711 A1 2/2004

OTHER PUBLICATIONS

Tomasko, D. L. et al., "Tailoring of Specific Interactions to Modify the Morphology of Naproxen" Journal of Crystal Growth, vol. 205, pp. 233-243, Aug. 15, 1999.
Muscara, M. N. et al. "Antihypertensive Properties of a Nitric Oxide-Releasing Naproxen Derivative in Two-Kidney, One-Clip Rats", Am J Physiol Heart Circ Physiol, vol. 279, pp. H528-H535, Aug. 1, 2000.
Gordan, M. S. et al., "Manipulation of Naproxen Particle Morphology Via the Spherical Crystallization Technique to Achieve a Directly Compressible Raw Material", Drug Development and Industrial Pharmacy, vol. 18, No. 8, pp. 1279-1290, Jan. 1, 1990.

*Primary Examiner* — KIristin Bianchi
(74) *Attorney, Agent, or Firm* — Arent Fox LLP

(57) ABSTRACT

The present invention relates to a method for purifying naproxcinod comprising the steps of:
a) dissolving or dispersing a mixture containing naproxcinod in an amount higher than 90% by weight in a solvent;
b) cooling the solution or two phases dispersion under stirring to a temperature ranging from −20° C. to 10° C.
c) optionally seeding the solution with crystals of naproxcinod
d) stirring, by maintaining the temperature in the range from −40° C. to 10° C.
e) collecting the formed solid by maintaining the temperature under 15° C.

A further object of the invention is a crystalline form of naproxcinod.

10 Claims, No Drawings

METHOD FOR PURIFYING 4-(NITROOXY)BUTYL(2S)-2-(6-METHOXY-2-NAPHTHYL) PROPANOATE

CROSS-REFERENCE TO RELATED APPLICATIONS

This application is a National Stage entry of International Application No. PCT/IB2009/006382, filed Jun. 18, 2009, which claims priority to Italian Patent Application No. RM2008A000325, filed Jun. 20, 2008. The disclosure of the prior application is hereby incorporated in its entirety by reference.

The present invention relates to a method for purifying naproxcinod and to naproxcinod in crystalline form.

Naproxcinod is 4-(nitrooxy)butyl (2S)-2-(6-methoxy-2-naphthyl)propanoate, known also as HCT 3012.

Naproxcinod is a nitric oxide (NO)-releasing derivative of naproxen with reduced gastrointestinal and cardiovascular toxicity. Naproxcinod is in Phase III clinical trials for treatment of signs or symptoms of osteo-arthrite.

WO 01/10814 discloses a process for preparing naproxcinod by reacting (2-(S)-(6-methoxy-2-naphtyl)-propionyl chloride with 4-nitrooxybutan-1-ol in methylene chloride, in the presence of potassium carbonate.

Naproxcinod is an oil at room temperature and the purification of large scale quantities of the compound is difficult and very expensive.

It has now surprisingly found that naproxcinod can be obtained in a crystalline form at low temperature.

An object of the present invention is a method for purifying naproxcinod, the method comprising the steps of:
a) dissolving or dispersing a mixture containing naproxcinod in a solvent;
b) cooling the solution or two phases dispersion under stirring to a temperature ranging from −20° C. to 10° C.;
c) optionally seeding the solution with crystals of naproxcinod
d) stirring, by maintaining the temperature in the range from −40° C. to 10° C.;
e) collecting the formed solid by maintaining the temperature under 15° C.;

Preferably the mixture of step a contains naproxcinod in an amount higher than 90% by weight.

The solvent of step a) is a solvent able to dissolve naproxcinod or form a two phases dispersion (oily phase of naproxcinod containing the solvent dispersed in a solution of naproxcinod in the solvent). The solvent may be a polar or apolar aprotic solvent or a polar protic solvent. The aprotic solvent may be an alkane, ester, ketone, such as for example n-exane, acetone, toluene or THF, or a mixture thereof.

Preferably the solvent is a polar protic solvent such as alcohols, diols, primary amides or a mixture thereof. Particularly preferred are $C_1$-$C_4$ aliphatic alcohol such as methanol, ethanol, isopropanol or 1-butanol, diols such as diethylenglycol, or primary amides such as formamide or a mixture thereof.

The temperature of step b) is preferably in the range from −15° C. to 5° C.

The temperature of step d) is preferably in the range from −15° C. to 5° C.

The temperature of step e) is preferably under 10° C.

A further object of the present invention is the product obtained by the described process.

An object of the invention is the crystalline form of naproxcinod having a melting point of about 15° C.

The present method is effective for purifying either naproxcinod of high purity (≧99%) or of a lower purity (≧90%-99%) obtained by different processes.

Naproxcinod produced by the process described in WO 01/10814 may contain impurities such as:
Naproxen (S)-2-(6-methoxy-2-naphthyl) propionic acid
HCT 3013: 4-hydroxybutyl (S)-2-(6-methoxy-2-naphthyl) propanoate
NapOMe: Methyl (S)-2-(6-methoxy-2-naphthyl) propanoate
HCT 3016: 4-chlorobutyl (S)-2-(6-methoxy-2-naphthyl) propanoate
BDMN: 1,4-butanediol mononitrate
BDDN 1,4-butanediol dinitrate
(4-methanesulfonyloxy)butyl(2S)-2-(6-methoxy-2-naphtyl)propanoate ("Mesyl derivative") may be present in naproxcinod produced by the method reported in WO 03/045896.

The method provides for the optional addition, at the selected temperature, of naproxcinod crystallization seeds to stirred crystallization mixture; the addition induces the immediate crystallization of the mixture.

Generally, the solid product is isolated by filtration, at the crystallization temperature, after having kept the crystallization mixture at the temperature of choice for 0.5-30 hours, the preferred time range being from 3 to 12 hours. Solvated solid naproxcinod (wet powder), is isolated by filtration, at the crystallization temperature, and washed with small amount of pre-cooled solvent.

Different work up procedures are used to isolate unsolvated, solvent free, purified naproxcinod either as dry powder or as oily compound:
a) The solvated solid is dissolved in a suitable inert solvent ($CH_2Cl_2$, toluene etc.) and washed with water. Evaporation of the solvent at room temperature in vacuo provides purified naproxcinod as solvent free oily residue.
b) The solvated solid is melted at circa 15° C. and the solvent removed in vacuo to provide solvent free purified naproxcinod as an oily residue.
c) The solvated solid is converted into unsolvated solid by keeping the initially solvated solid in vacuo at a temperature lower than the melting point. Purified oily naproxcinod is obtained by heating the dry product at the melting point.

Mother liquors by in vacuo concentration provide quantitative recovery of naproxcinod, with purity lower than that of the starting naproxcinod.

No new impurities or increase of the existing ones were revealed, by HPLC analysis, under a large variety of crystallization conditions.

BDMN and BDDN were found to be quantitatively accumulated in the mother liquors.

The practical consequence of the observed stability of naproxcinod and of the impurities is that a virtually quantitative yield of the crystallized product as naproxcinod can be recovered from the crystallization mother liquors and re-used.

The purification efficacy depends mainly on the nature of the impurities and of the solvent.

The ratio between naproxcinod and solvents/diluents depends on the nature of solvent/diluent, impurities, their content, the purity of starting naproxcinod and on the purity target.

The turbulence, provoked by the stirring in a given reactor, of the crystallization system does not affect efficacy of purification.

Protic polar solvents (alcohols, diols, primary amides) are the preferred solvents for the purification of naproxcinod, by solution and by two phases system, contaminated by polar impurities such as Naproxen, Naproxen methyl ester, HCT 3013, BDMN and BDDN.

Generally, the content of polar contaminants, are reduced to ⅕-⅒ with respect to the original quantity, more polar impurities such as BDMN and BDDN are completely removed.

Primary and secondary alcohols (methanol, ethanol, 2-propanol, 1-butanol), diols (diethylenglycol) and primary amides (formamide) as well as their mixtures were tested successfully. When the purification is carried out in methanol solution, yields increase by lowering crystallization temperature, from −15° C. to −25° C., without affecting the purification efficacy.

Solution method by using formamide as solvent and two phases method by using diethylenglycol behave similarly and show an efficacy close to that obtained by alkyl alcohols.

As the solution method starts with the dissolution of naproxcinod in a protic solvent, at a given temperature, the yield and productivity are mainly dictated by naproxcinod solubility in the solvent.

Once the oily naproxcinod is dissolved, the solution (in $CH_3OH$) remains clear also when it is cooled down below the crystallization temperature.

Two phases method is characterized by much higher productivity which is influenced by the purity target. In principle, productivity (quantity/volume) could approach 100%, the ideal solvent should have high affinity toward impurities and low affinity toward naproxcinod.

Crystallization in solution (at a lower temperature) and in two phases (at a higher temperature) provides similar purification efficacy and yields, the two phases system being much more productive (quantity/volume). At the same temperature, two phases purification efficacy is slightly lower and can be enhanced, without significant loss in productivity, by increasing crystallization temperature Two phases system carried out at different temperatures by using 1 part of naproxcinod and 2 parts of $CH_3OH$, provide productivity as high as 19-29% and yields 56-88%.

The two phases method is the method of choice showing good yields, very high productivity and reasonable efficacy.

Polar impurities such as BDMN and BDDN were removed and found to be accumulated in the mother liquors.

For most of the investigated crystallization in solution, the yield ranged from 50% to 90%, and productivity from 4% to 10%. Polar protic solvents can be used in combination with aprotic polar solvents to influence the efficacy of the crystallization.

Crystallization can be induced also in non homogeneous conditions where naproxcinod is present as an insoluble oil as a component of an emulsion system.

Water may be used in combination with polar solvents successfully.

Powder XRD patterns of all the analysed samples (wet solid A and dry solid B) obtained by crystallization from methanol, ethanol, isopropanol and from neat HCT 3012 are perfectly comparable, indicating the presence of the same crystal phase in all the samples, independently from the solvent used in the crystallization process and from wet or dry indications. Only small variations of the relative intensity, consistent with different degree of preferential orientation, produced in the sample preparation, were observed in the experimental patterns, whereas the peak positions were found to be reproducible within the experimental errors. Both the dry and wet crystalline HCT 3012 were analysed as far as solvent content and purity. DSC of samples from methanol as well as the product crystallized from neat shows very similar onset temperature (about 13° C.).

EXPERIMENTAL PROCEDURE

In the following experimental part naproxcinod is reported as HCT 3012.

Example 1

Reagents and Equipment

Reagents: Different samples were prepared mixing pure HCT 3012 and known amount of impurities (HCT 3013 or HCT 3016 or the mesyl derivative). For seeding, a sample of high purity Naproxcinod was used.

This sample was obtained crystallizing three times a sample of Naproxcinod with methanol. The sample was stored at −18° C.

Equipment: Trials were performed in a closed jacketed, 1 L glass reactor equipped with mechanical stirring. For filtration, a jacketed filter was used.

i) Crystallization from Alcohols

Two trials have been performed: the first one in methanol and the other in isopropanol. The crude HCT 3012 lots submitted to the trials contained a variable amount of the HCT 3013 as the main impurity.

Description of the procedure. 30 g of HCT 3012 were mixed with 120 mL of the alcohol: a two phase system was formed (an oily phase dispersed in the solvent). The mixture was cooled under stirring, seeded, stirred 1 hour in order to induce nucleation and crystals growth then cooled again at −10° C. The mixture was kept at this temperature for at least 1 hour and then the solid was collected by filtration using a cooled jacketed filter. Solvent is removed by heating under vacuum. Table 1 shows the purification effect: HCT 3013 was reduced from 0.9 to 0.1

[HPLC analysis, area %] by methanol (trial a) and from 0.6 to 0.2 by isopropanol (trial b)

TABLE 1

Crystallization of HCT 3012 in the presence of alcohols

| Solvent | Seeding T [° C.] | Impurity | Impurity content before crystallization [HPLC, area %] | Impurity content after crystallization [HPLC area %] |
|---|---|---|---|---|
| Methanol | 5 | HCT 3013 | 0.9 | 0.1 |
| Isopropanol | 7 | HCT 3013 | 0.6 | 0.2 | ii) Crystallization from Acetone/Methanol or Acetone/Isopropanol

Two trials were performed as follows: HCT 3012 was first mixed with acetone and then the homogenous liquid was added drop-wise to the alcohol. The material used for these trials had the HCT 3013 as the main impurity.

Description of the procedure. 30 g of Naproxcinod were mixed with 10 mL of acetone at room temperature. The solution was added drop-wise in about 30 min to the alcohol kept under stirring at −10° C. (120 mL of methanol in trial c, 120 mL of isopropanol in trial d): the product precipitated immediately. The suspension was stirred for at least 1 hour at −10° C. and than filtered on a cooled jacketed filter obtaining a white, fine and homogenous solid. The solvent was removed by heating under vacuum.

Table 2 summarizes the results of these experiments. In both trials HCT 3013 was reduced from 0.6 to 0.2%, but a higher yield were obtained using isopropanol.

TABLE 2

Trials carried out slowly adding a HCT 3012/acetone mixture to the cold alcohol

| Solvent | Temperature [° C.] | Impurity | Impurity content before crystallization [HPLC, area %] | Impurity content after crystallization [HPLC area %] |
|---|---|---|---|---|
| Methanol/acetone | −10 | HCT 3013 | 0.6 | 0.2 |
| Isopropanol/acetone | −10 | HCT 3013 | 0.6 | 0.2 | iii) Crystallization from Isopropanol/Acetone or Isopropanol/THF as Solvents

A set of experiments was performed crystallizing HCT 3012 from isopropanol containing either THF or acetone. For these trials a sample of HCT 3012 containing HCT 3013, HCT 3016 and the mesyl derivative as impurities was prepared on purpose.

Description of the procedure. 30 g of HCT 3012 were dissolved in the crystallization solvent (a solution was obtained at room temperature). The solution was cooled down to the seeding temperature (from 0 to −10° C., in this range a two-phases liquid is observed). After seeding, the mixture was stirred at the same temperature for at least 1 hour. Then it was cooled at −10/−15° C. and the crystallized solid collected by filtration using a cooled jacketed filter. Solvent was removed by heating under vacuum.

The analytical results of the above trials are gathered in Table 3.

TABLE 3

| Solvent | Seeding T [° C.] | Impurity | Impurity content before crystallization [HPLC, area %] | Impurity content after crystallization [HPLC area %] |
|---|---|---|---|---|
| IPA (100 mL) + acetone (10 mL) | −5 | HCT 3013 | 0.6 | 0.2 |
| IPA (100 mL) + THF (10 mL) | −2 | HCT 3013 | 0.6 | 0.2 |
| IPA (100 mL) + acetone (10 mL) | −4 | Mesyl derivative | 0.4 | 0.4 |
| IPA (200 mL) + THF (20 mL) | 0 | Mesyl derivative | 0.4 | 0.2 |
| IPA (200 mL) + THF (20 mL) | 0 | Mesyl derivative | 1.0 | 0.7 |
| IPA (100 mL) + acetone (10 mL) | −10 | HCT 3016 | 0.6 | 0.4 |
| IPA (100 mL) + THF (10 mL) | −5 | HCT 3016 | 0.6 | 0.4 |
| IPA (200 mL) + THF (20 mL) | 0 | HCT 3016 | 0.6 | 0.3 |
| IPA (200 mL) + THF (40 mL) | −10 | HCT 3016 | 0.6 | 0.3 |
| IPA (200 mL) + THF (20 mL) | 0 | HCT 3016 | 0.3 | 0.1 | iv) Crystallization from Isopropanol/THF

A saturated solution of HCT 3012 in isopropanol/THF was seeded and stirred at 0° C. until a relevant amount of crystallized product was observed (nucleation). A solution of HCT 3012 in isopropanol/THF was then slowly added and the mixture was carefully monitored in order to avoid the formation of liquid HCT 3012. In other words, the rate of addition was adjusted to have only solid product dispersed in the solvent. The results are summarized in table 4.

Description of the procedure. 17 g of HCT 3012 are dissolved at 0° C. in a mixture of 200 mL of isopropanol and 20 mL of THF. A turbid solution is obtained. After seeding, the mixture is maintained at this temperature for at least 1 hour. In the meantime, 43 g of HCT 3012 are dissolved at 30° C. in a mixture of 200 mL of isopropanol and 20 mL of THF.

This solution, kept at 30° C. is added dropwise in about 4 hours to the previously seeded mixture.

The mixture is then cooled again at −10/−15° C. and the crystallized solid is collected by filtration using a cooled jacketed filter. The solid is washed with isopropanol at −15° C. The solvent is eventually removed under vacuum.

TABLE 4

| Solvent | Seeding T [° C.] | Impurity | Impurity content before crystallization [HPLC, area %] | Impurity content after crystallization [HPLC area %] |
|---|---|---|---|---|
| IPA (400 mL) + THF (40 mL) | 0 | HCT 3016 | 0.2 | 0.1 |
| IPA (400 mL) + THF (40 mL) | −3 | Mesyl derivative | 1.0 | 0.7 | v) Synthesis of Impurities 4-chlorobutyl (2S)-2-(6-methoxy-2-naphtyl)propanoate HCT 3016

Structure:

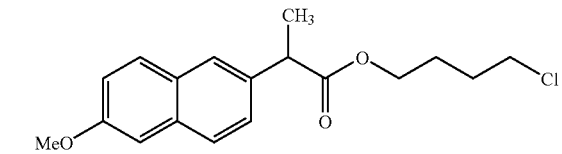

Preparation: 30 g of Naproxen chloride are dissolved in 120 g of dichloromethane. This solution is cooled at 0° C. and a solution of 14.5 g of 1-chloro-3-buthanol in 100 g of dichloromethane is added dropwise in 2 hours. After a completion time of 3 hours at 0° C., 60 g of water are added and is the mixture is stirred for 10 hours. After phase separation, 60 g of water are added to organic phase and the mixture is stirred for 10 hours. After phase separation, the organic phase is concentrated to 120 mL and 4.5 g of potassium carbonate are added. The mixture is refluxed at about 40° C. for 4 hours. After filtration and vacuum concentration, an oil is obtained (HPLC purity 90%).

(4-hydroxybutyl) (2S)-2-(methoxy-2-naphtyl)propanoate HCT 3013

Structure:

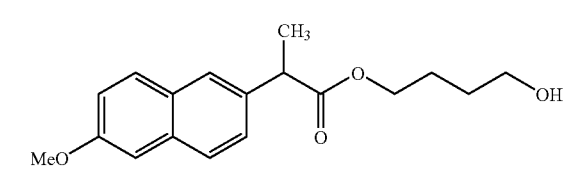

Preparation based on patent WO 03/045896: 50 g of (S)—Naproxen are mixed with 196 g of 1,4-butanediol and the stirred mixture to is heated at 80° C. 0.42 g of sulfuric acid are added and the resulting mixture is stirred at 80° C. for 6.5 hours. After cooling at 50° C., toluene (33 g), water (35 g) and hexane (67 g) are added and the resulting two phase-system is stirred for 30 min. After phase separation, toluene (25 g) and hexane (25 g) are added to the aqueous layer at 50° C. The two phase system is stirred for 15 min. After phase separation, the aqueous layer is again extracted twice with toluene (25 g) and hexane (25 g). Toluene (130 g) and 0.2 M aqueous potassium carbonate (149 g) are added to the aqueous layer at 50° C. and the resulting two phase system is stirred for 30 min before phase separation. Water (150 g) is added to the organic layer and the resulting two phase system is stirred for 15 min before phase separation. This extraction is repeated again, with 150 g of water. The organic phase is evaporated under vacuum to get an oily residue. The HPLC purify of the product is 99%.

(4-methanesulfonyloxy)butyl(2S)-2-(6-methoxy-2-naphtyl)propanoate "Mesyl derivative"

Structure:

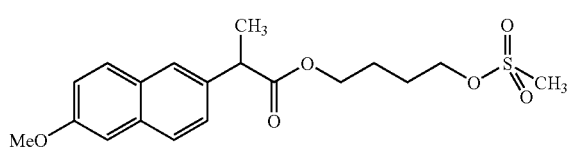

Preparation based on patent WO 03/045896: (4-hydroxybutyl)(2S)-2-(6-methoxy-2-naphtyl)propanoate (8.4 g), methanesulfonyl chloride (3.7 g) and toluene (40 mL) are charged in a round bottomed flask. Triethylamine (3.0 g) is added dropwise to the solution; the temperature spontaneously increased to 60° C. during the addition. The precipitation of some solid matter occurs and toluene (40 mL) is added to facilitate the stirring. The reaction mixture is stirred at room temperature for 3 days. 1M HCl (30 mL) is added and the mixture is heated to 60° C. to dissolve the solid. After phase separation at 60° C., the organic phase is slowly diluted with n-heptane (50 mL) at 50° C. Upon cooling at room temperature the product crystallizes. After filtration, it is dried under vacuum at 30° C. to get a solid product having HPLC purity of 99%. The $^1$H-NMR spectrum confirmed the structure.

Example 2

Example 2 Comprises Experiments 01-52

ANALYTICAL METHOD: HPLC
Column: YMC Pack ODS-AQ, 150 mm length, 4.6 mm diameter, 5 µm size
Column temperature: 30° C.
Mobile Phase:
A—Acetonitrile /MeOH /Water, mix and add 0.3 ml of TFA
B—Acetonitrile and 0.3 ml of TFA
Gradient Composition

| Time (min) | % A | % B |
|---|---|---|
| 0.0 | 100 | 0 |
| 63.0 | 100 | 0 |
| 86.0 | 10 | 90 |
| 93.0 | 10 | 90 |
| 94.0 | 100 | 0 |

Total Analysis Time 102 min

| Mobile phase flow: | 0.6 ml/min |
|---|---|
| Injection volume: | 10 µl |
| Detection: | FLD, 232 nm (excitation), 350 nm (emission) VWD at 210 and 232 nm |
| Calculations: | external standard |

Preparation of Crystallization Seeds (Experiment 01)

| HCT 3012 (g) | Solvent/diluent (g) | Crystallization temperature (° C.) | Time (hours) | % Yield |
|---|---|---|---|---|
| lot # US07600379 (4.95) | CH$_3$OH Lot # VWR08Z0365 (50) | −15 | 1 | — |

Seeds of HCT 3012 have been prepared as described in experiment 02 for solid B.

Analytical Results of Experiment 01

| | Naproxen (%) | HCT 3013 (%) | NapOMe (%) | HCT3016 (%) | BDMN (%) | BDDN (%) |
|---|---|---|---|---|---|---|
| Starting | 0.052 | 0.017 | 0.016 | 0.021 | 0.090 | nq |
| Solid A | 0.006 | 0.004 | 0.015 | 0.014 | nd | nd |
| Solid B | 0.07 | 0.005 | 0.015 | 0.013 | nd | nd |

Crystallization from Methanol without Seeding (Experiment 02)

| HCT 3012 (g) | Solvent/diluent (g) | Crystallization temperature (° C.) | Time (hours) | % Yield |
|---|---|---|---|---|
| lot # US07600379 (5.10) | CH$_3$OH Lot # VWR08Z0365 (51) | −15 | 3 | 54.1 |

HCT 3012 (U.S. Pat. No. 7,600,379; 5.10 g) and methanol (VWR 08Z2128; 51 g) are charged into a three necks 100 ml glass jacketed reactor under nitrogen and under magnetic stirring. The heterogeneous mixture is kept under stirring at room temperature for the time (10 minutes) required to get a clear solution. The solution is cooled down to −15° C. (crystallization temperature) and is kept at this temperature under stirring for 15 minutes. The solution remains clear. After 20 minutes no precipitate as solid or oily material is separated. Scratching by a spatula, the solution becomes cloudy and crystals start to separate; no increase in temperature is observed.

The heterogeneous mixture is stirred at −15° C. for 3 hrs and then filtered through a 150 ml jacketed filter keeping the jacket at about −20° C. The cake is washed with pre cooled (−20° C.) methanol (20 g) and the wet solid is compressed with a pre cooled (−20° C.) stopper.

The solid material is collected into a pre cooled (−20° C.). 50 ml bottom flask and kept at −20° C.: 5.11 g of wet solid (solid A) are obtained.

A sample of solid A is analysed by HPLC showing 54.0% of HCT 3012. Consequently the wet solid contains 2.76 g of HCT 3012 and 2.35 g of methanol by difference; yield 54.1%.

2.33 g of the wet solid are dried under vacuum (residual pressure 0.1 mmHg) at −15° C. to provide after 6 hours 1.13 g of a sample containing 1.02 g of HCT 3012 (solid B) and 0.11 g of methanol by difference.

Analytical Results of Experiment 02

| | Naproxen (%) | HCT 3013 (%) | NapOMe (%) | HCT3016 (%) | BDMN (%) | BDDN (%) |
|---|---|---|---|---|---|---|
| Starting | 0.052 | 0.017 | 0.016 | 0.021 | 0.090 | nq |
| Solid A | 0.016 | 0.006 | 0.008 | 0.016 | nd | nd |
| Solid B | 0.016 | 0.006 | 0.008 | 0.013 | nd | nd |

3.3.2.3. Crystallization from Methanol with Seeding at −5° C. (Experiment 03)

| HCT 3012 (g) | Solvent/diluent (g) | Crystallization temperature (° C.) | Time (hours) | % Yield |
|---|---|---|---|---|
| lot # US07600379 (12.71) | CH₃OH Lot # VWR08Z0365 (127) | −5 | 3 | 42.2 |

HCT 3012 (U.S. Pat. No. 7,600,379; 12.71 g) and methanol (VWR 08Z2128; 127 g) are charged into a three necks 250 ml glass jacketed reactor under nitrogen and under mechanical stirring. The heterogeneous mixture is kept under stirring at room temperature for the time (10 minutes) required to get a clear solution. The solution is cooled down to −5° C. (crystallization temperature) and kept at this temperature under stirring for 10 minutes. The solution remains clear. After additional 20 minutes the clear solution is added with about 1-2 mg of HCT 3012/01 seed (solid A). After about 2-3 minutes crystals start to separate. The heterogeneous mixture is stirred at −5° C. for 3 hrs and then filtered through a 150 ml jacketed filter keeping the jacket at about −20° C. The cake is washed with pre cooled (−20° C.) methanol (50 g) and the wet solid is compressed with a pre cooled (−20° C.) stopper.

The solid material is collected into a pre cooled (−20° C.). 50 ml bottom flask and kept at −20° C.: 6.84 g of wet solid (solid A) are obtained.

A sample of solid A is analysed by HPLC showing 78.4% of HCT 3012. Consequently the wet solid contains 5.36 g of HCT 3012 and 1.48 g of methanol by difference; yield 42.2%.

3.12 g of the wet solid are dried under vacuum (residual pressure 0.1 mmHg) at −15° C. to provide after 6 hours 1.86 g of a sample containing 1.74 g of HCT 3012 (solid B, corresponding to a 30.0%) and 0.12 g of methanol by difference.

The methanolic mother liquors are concentrated under vacuum at about 37° C. (external bath) to provide an oily residue (7.59 g).

Analytical Results of Experiment 03

| | Naproxen (%) | HCT 3013 (%) | NapOMe (%) | HCT3016 (%) | BDMN (%) | BDDN (%) |
|---|---|---|---|---|---|---|
| Starting | 0.052 | 0.017 | 0.016 | 0.021 | 0.090 | nq |
| Solid A | 0.012 | 0.004 | 0.006 | 0.012 | nd | nd |
| Solid B | 0.011 | 0.003 | 0.006 | 0.015 | nd | nd |
| Mother liquors | 0.089 | 0.027 | 0.037 | 0.032 | 0.201 | 0.088 |

Crystallization from Methanol with Seeding at −15° C. (Experiment 04)

| HCT 3012 (g) | Solvent/diluent (g) | Crystallization temperature (° C.) | Time (hours) | % Yield |
|---|---|---|---|---|
| lot # US07600379 (20.19) | CH₃OH Lot # VWR08Z0365 (202) | −15 | 15 | 66.5 |

HCT 3012 (U.S. Pat. No. 7,600,379; 20.19 g) and methanol (VWR 08Z2128; 202 g) are charged into a three necks 500 ml glass jacketed reactor under nitrogen and under mechanical stirring. The heterogeneous mixture is kept under stirring at room temperature for the time (10 minutes) required to get a clear solution. The solution is cooled down to −15° C. (crystallization temperature) in about 30 minutes and kept at this temperature under stirring for 20 minutes. The solution remains clear. After 20 minutes the clear solution is added with about 1-2 mg of HCT 3012/01 seed (solid B). After about 2-3 minutes, crystals start to separate. The heterogeneous mixture is stirred at −5° C. for 15 hrs and then filtered through a 150 ml jacketed filter keeping the jacket at about −20° C. The cake is washed with pre cooled (−20° C.) methanol (18 g) and the wet solid is compressed with a pre cooled (−20° C.) stopper.

The solid material is collected into a pre cooled (−20° C.) 50 ml bottom flask and kept at −20° C.: 15.73 g of wet solid (solid A) are obtained.

A sample of solid A is analysed by HPLC showing 85.4% of HCT 3012. Consequently the wet solid contains 13.43 g of HCT 3012 and 2.30 g of methanol by difference; yield 66.5%.

3.61 g of the wet solid are dried under vacuum (residual pressure 0.1 mmHg) at −15° C. to provide after 6 hours 3.46 g of a sample containing 3.01 g of HCT 3012 (solid B, corresponding to a 64.7%) and 0.60 g of methanol by difference.

Methanolic mother liquors are concentrated under vacuum at about 37° C. (external bath) to provide an oily residue of 7.69 g, which is dissolved in methylene chloride (19 g). The organic phase is washed three times with 17, 17 and 16 g of water respectively. The organic phase is concentrated under vacuum (external bath at 37° C.), obtaining 7.37 g.

Analytical Results for Experiment 04

| | Naproxen (%) | HCT 3013 (%) | NapOMe (%) | HCT3016 (%) | BDMN (%) | BDDN (%) |
|---|---|---|---|---|---|---|
| Starting | 0.052 | 0.017 | 0.016 | 0.021 | 0.090 | nq |
| Solid A | 0.012 | 0.004 | 0.007 | 0.011 | nd | nd |
| Solid B | 0.011 | 0.005 | 0.007 | 0.014 | nd | nd |
| Mother liquors | 0.104 | 0.038 | 0.042 | 0.036 | 0.090 | 0.115 |

Crystallization from Ethanol with Seeding at −15° C. (Experiment 05)

| HCT 3012 (g) | Solvent/diluent (g) | Crystallization temperature (° C.) | Time (hours) | % Yield |
|---|---|---|---|---|
| lot # US07600379 (20.20) | CH$_3$CH$_2$OH Lot # FK1337350 (202) | −15 | 15 | 77.3 |

HCT 3012 (U.S. Pat. No. 7,600,379; 20.20 g) and ethanol (FK1337350; 202 g) are charged into a three necks 500 ml glass jacketed reactor under nitrogen and under mechanical stirring. The heterogeneous mixture is kept under stirring at room temperature for the time (20 minutes) required to get a clear solution. The solution is cooled down: at −3° C. the solution become cloudy (two phase system oily material and solution), at −10° C. oily material is separated. The mixture is heated up to +20° C., then cooled down until −5° C. (crystallization temperature) in about 30 minutes and kept at this temperature under stirring for 20 minutes. The solution remains clear. After 20 minutes the clear solution is added with about 1-2 mg of HCT 3012/01 seed (solid B). After about 2-3 minutes, crystals start to separate. The heterogeneous mixture is cooled down and stirred at −15° C. for hrs and then filtered through a 150 ml jacketed filter keeping the jacket at about −20° C. The cake is washed with pre cooled (−20° C.) ethanol (20 g) and the wet solid is compressed with a pre cooled (−20° C.) stopper.

The solid material is collected into a pre cooled (−20° C.) 50 ml bottom flask and kept at −20° C.: 22.44 g of wet solid (solid A) are obtained.

A sample of solid A is analysed by HPLC showing 69.6% of HCT 3012. Consequently the wet solid contains 15.62 g of HCT 3012 and 6.82 g of ethanol by difference; yield 77.3%.

3.75 g of the wet solid are dried under vacuum (residual pressure 0.1 mmHg) at −15° C. to provide after 6 hours 2.17 g of HCT 3012 (solid B) containing 0.04% of ethanol. Powder XRD pattern is perfectly comparable to the one reported in table no. 1 of experimental section for HCT 3012 prepared in example). 49). DSC analysis, carried out as reported in the experimental section, has shown the onset at 13.06° C.

Ethanolic mother liquors are concentrated under vacuum at about 37° C. (external bath) to provide an oily residue of 5.45 g, which is dissolved in methylene chloride (120 g). The organic phase is washed with water (3×100 ml). The organic phase is concentrated under vacuum (external bath at 37° C.), obtaining 5.00 g.

Analytical Results for Experiment 05

| | Naproxen (%) | HCT 3013 (%) | NapOMe (%) | HCT3016 (%) | BDMN (%) | BDDN (%) |
|---|---|---|---|---|---|---|
| Starting | 0.052 | 0.017 | 0.016 | 0.021 | 0.090 | nq |
| Solid A | 0.016 | 0.005 | 0.007 | 0.014 | nd | nd |
| Solid B | 0.015 | 0.005 | 0.007 | 0.015 | nd | nd |
| Mother liquors | 0.100 | 0.037 | 0.041 | 0.040 | 0.254 | 0.166 |

Crystallization from Isopropanol with Seeding at −15° C. (Experiment 06)

| HCT 3012 (g) | Solvent/diluent (g) | Crystallization temperature (° C.) | Time (hours) | % Yield |
|---|---|---|---|---|
| lot # US07600379 (10.06) | IPA Lot # K38782434-825 (101) | −15 | 4 | 64.5 |

HCT 3012 (U.S. Pat. No. 7,600,379; 10.06 g) and isopropanol (K38782434-825; 101 g) are charged into a three necks 250 ml glass jacketed to reactor under nitrogen and under mechanical stirring. The heterogeneous mixture is kept under stirring at room temperature for 20 minutes and it remain heterogeneous. The temperature of the mixture is raised to +30° C., causing the mixture to become a clear solution. The temperature of the solution is cooled to +25° C., and the solution start to become heterogeneous again. Isopropanol (20 g) is added to the mixture, with evident solubilization of the oily material. The temperature of the mixture is cooled down to +20° C. and then to 0° C. and kept under this condition for 15 hours: no crystallization occurs. The two phase system (oil and solvent) is cooled to −3° C. and 1-2 mg of seeding crystals (HCT 3012/01 seed, solid A) are added. Scratching by a spatula, the solution becomes cloudy and crystals start to separate. The reaction mixture is cooled down to −15° C. and kept under stirring and under nitrogen for 4 hours.

The mixture is filtered through a 150 ml jacketed filter keeping the jacket at about −20° C. The cake is washed with pre cooled (−20° C.) isopropanol (20 g) and the wet solid is compressed with a pre cooled (−20° C.) stopper.

The solid material is collected into a pre cooled (−20° C.) 50 ml bottom flask and kept at −20° C.: 10.29 g of wet solid (solid A) are obtained.

A sample of solid A is analysed by HPLC showing 63.0% of HCT 3012. Consequently the wet solid contains 6.48 g of HCT 3012 and 3.81 g of isopropanol by difference; yield 64.5%. (In a parallel experiment the wet solid A, containing 57% of isopropanol, was analysed by PXRD. Powder XRD pattern is perfectly comparable to the one reported in table no. 1 of experimental section for HCT 3012 prepared in example 49).

3.19 g of the wet solid are dried under vacuum (residual pressure 0.1 mmHg) at −15° C. to provide after 6 hours 2.45 g of a sample containing 2.20 g of HCT 3012 (solid B, corresponding to a 64.3%) and 0.25 g of isopropanol by difference. (In a parallel experiment a sample is dried at 0.1 mmHg at 15° C. The sample contain 1.5% of isopropanol. Powder XRD pattern is perfectly comparable to the one reported in table no. 1 of experimental section for HCT 3012 prepared in example 49).

Isopropanolic mother liquors are concentrated under vacuum at about 37° C. (external bath) to provide an oily residue of 2.02 g, which is dissolved in methylene chloride (36 g). The organic phase is washed with water (3×100 ml). The organic phase is concentrated under vacuum (external bath at 37° C.), obtaining 1.78 g.

Analytical Results for Experiment 06

| | Naproxen (%) | HCT 3013 (%) | NapOMe (%) | HCT3016 (%) | BDMN (%) | BDDN (%) |
|---|---|---|---|---|---|---|
| Starting | 0.052 | 0.017 | 0.016 | 0.021 | 0.090 | nq |
| Solid A | 0.011 | 0.003 | 0.007 | 0.016 | nd | nd |
| Solid B | 0.012 | 0.003 | 0.007 | 0.016 | nd | nd |
| Mother liquors | 0.129 | 0.075 | 0.048 | 0.057 | 0.251 | 0.187 |

Crystallization from Methanol with Seeding at −25° C. Experiment 07)

| HCT 3012 (g) | Solvent/diluent (g) | Crystallization temperature (° C.) | Time (hours) | % Yield |
|---|---|---|---|---|
| lot # US07600379 (10.04) | CH₃OH Lot # VWR08Z0365 (101) | −25 | 15 | 82.1 |

HCT 3012 (U.S. Pat. No. 7,600,379; 10.04 g) and methanol (VWR 08Z2128; 101 g) are charged into a three necks 250 ml glass jacketed reactor under nitrogen and under mechanical stirring. The heterogeneous mixture is kept under stirring at room temperature for the time (20 minutes) required to get a clear solution. The solution is cooled down to −3° C. and kept at this temperature under stirring for 15 minutes. The solution remains clear. After 20 minutes the clear solution is added with about 1-2 mg of HCT 3012/01 seed (solid B). After about 2-3 minutes crystallization starts. The heterogeneous mixture is cooled down to −25° C., stirred for 15 hrs and then filtered through a 150 ml jacketed filter keeping the jacket at about −20° C. The cake is washed with pre cooled (−20° C.) methanol (12 g) and the wet solid is compressed with a pre cooled (−20° C.) stopper. The solid material is collected into a pre cooled (−20° C.). 50 ml bottom flask and kept at −20° C.: 10.30 g of wet solid solid A) are obtained.

A sample of solid A is analysed by HPLC showing 80.0% of HCT 3012. Consequently the wet solid contains 8.24 g of HCT 3012 and 2.06 g of methanol by difference; yield 82.1%.

Analytical Results for Experiment 07

| | Naproxen (%) | HCT 3013 (%) | NapOMe (%) | HCT3016 (%) | BDMN (%) | BDDN (%) |
|---|---|---|---|---|---|---|
| Starting | 0.052 | 0.017 | 0.016 | 0.021 | 0.090 | nq |
| Solid A | 0.013 | 0.005 | 0.007 | 0.017 | nd | nd |

Crystallization from Methanol/Water 95/5 (Experiment 08)

| HCT 3012 (g) | Solvent/diluent (g) | Crystallization temperature (° C.) | Time (hours) | % Yield |
|---|---|---|---|---|
| lot # US07600379 (10.08) | CH₃OH Lot # VWR08Z0365 (96) | −15 | 15 | 77.6 |

A solution of 5 g of demineralised water in methanol (VWR 08Z2128; 96 g) is cooled to −15° C. under nitrogen and under mechanical stirring. The solution is kept at −15° C. for 30 minutes, no water crystals are formed. The solution is warmed up at +20° C. and added with HCT 3012 (U.S. Pat. No. 7,600,379; 10.08 g). The heterogeneous mixture is kept under stirring at room temperature for the time (20 minutes) required to get a clear solution. The solution is cooled down, at +8° C. the solution becomes cloudy (oily emulsion), at −3° C. about 1-2 mg of HCT 3012/01 seed (solid B) are added. The emulsion is stirred at −3° C. for 15 minutes, then it is cooled down to −15° C. and kept under stirring for 15 hours. After this time a solid is formed and then filtered through a 150 ml jacketed filter keeping the jacket at about −20° C. The cake is washed with pre cooled (−20° C.) methanol (10 g) and the wet solid is compressed with a pre cooled (−20° C.) stopper.

The solid material is collected into a pre cooled (−20° C.). 50 ml bottom flask and kept at −20° C.: the wet solid consist of 7.59 g of fluffy crystals and 1.62 g of hard solid.

A sample of both solids is analysed by HPLC showing:
  82.4% of HCT 3012 fluffy crystals, corresponding to 6.25 g of HCT 3012 and 1.34 g of methanol/water by difference; yield 62.0%;
  96.5% of HCT 3012 hard solid, corresponding to 1.56 g of HCT 3012 and 0.06 g of methanol/water, yield 15.5%;
  total yield: 7.81 g, i.e. 77.5%.

Analytical Results for Experiment 08

| | Naproxen (%) | HCT 3013 (%) | NapOMe (%) | HCT3016 (%) | BDMN (%) | BDDN (%) |
|---|---|---|---|---|---|---|
| Starting | 0.052 | 0.017 | 0.016 | 0.021 | 0.090 | nq |
| Fluffy crystals | 0.011 | 0.005 | 0.009 | 0.017 | nd | nd |
| Hard solid | 0.007 | nq | 0.009 | 0.019 | nd | nq |

Repetition of Experiment 04 for Preparative Purposes (Experiment 09)

| HCT 3012 (g) | Solvent/diluent (g) | Crystallization temperature (° C.) | Time (hours) | % Yield |
|---|---|---|---|---|
| lot # US07600379 (20.03) | CH₃OH Lot # VWR08Z0365 (200) | −15 | 15 | 75.3 |

HCT 3012 (U.S. Pat. No. 7,600,379; 20.03 g) and methanol (VWR 08Z2128; 200 g) are charged into a three necks 500 ml glass jacketed reactor under nitrogen and under mechanical stirring. The heterogeneous mixture is kept under stirring at room temperature for the time (10 minutes) required to get a clear solution. The solution is cooled down to −15° C. (crystallization temperature) in about 30 minutes and kept at this temperature under stirring for 20 minutes. The solution remains clear. After 20 minutes the clear solution is added with about 1-2 mg of HCT 3012/01 seed (solid B). After about 2-3 minutes, crystals start to separate. The heterogeneous mixture is stirred at −15° C. for 15 hrs and then filtered through a 150 ml jacketed filter keeping the jacket at about −20° C. The cake is washed with pre cooled (−20° C.) methanol (18 g) and the wet solid is compressed with a pre cooled (−20° C.) stopper.

The solid material is collected into a pre cooled (−20° C.). 50 ml bottom flask and kept at −20° C.: 18.12 g of wet solid solid A) are obtained.

A sample of solid A is analysed by HPLC showing 83.3% of HCT 3012. Consequently the wet solid contains 15.09 g of HCT 3012 and 3.03 g of methanol by difference; yield 75.3%.
Analytical Results for Experiment 09

|  | Naproxen (%) | HCT 3013 (%) | NapOMe (%) | HCT3016 (%) | BDMN (%) | BDDN (%) |
|---|---|---|---|---|---|---|
| Starting | 0.052 | 0.017 | 0.016 | 0.021 | 0.090 | nq |
| Solid A | 0.008 | 0.003 | 0.006 | 0.015 | nd | nd |

Crystallization from Methanol of a Spiked Sample (Experiment 10)

| HCT 3012 (g) | Solvent/diluent (g) | Crystallization temperature (° C.) | Time (hours) | % Yield |
|---|---|---|---|---|
| lot # US07600379 (10.04) | CH$_3$OH Lot # VWR08Z0365 (101) | −15 | 15 | 64.5 |

The products listed hereunder are added to methanol (VWR 08Z2128; 101 g) previously charged into a three necks 250 ml glass jacketed reactor under nitrogen and under mechanical stirring:
  Naproxen (PM-7BB-KL, 100.4 mg)—the product dissolves, clear solution in obtained;
  NAPOMe (13560-2, 100.2 mg)—the product dissolves, clear solution in obtained;
  HCT 3013 (lot # 13567-2, 101.3 mg)—the product dissolves, clear solution in obtained;
  HCT 3015 (lot # 13530-5, 99.6 mg)—opalescent mixture;
  HCT 3012 (lot # U.S. Pat. No. 7,600,379, 10.03 g): the opalescent mixture become a clear solution after 15 minutes.
A sample is taken and analysed by HPLC to determine the composition.
The solution is cooled down to −3° C. and the solution becomes cloudy. 1-2 mg of HCT 3012/01 seed (solid B) are added and the mixture is stirred for additional 45 minutes, no crystalline solid formation is observed. The mixture temperature is lowered to −15° C. and kept at this condition under stirring for 15 hours. The heterogeneous mixture is filtered through a 150 ml jacketed filter keeping the jacket at about −20° C. The cake is washed with pre cooled (−20° C.) methanol (20 g) and the wet solid is compressed with a pre cooled (−20° C.) stopper.
The solid material is collected into a pre cooled (−20° C.). 50 ml bottom flask and kept at −20° C.: 8.92 g of wet solid (solid A) are obtained.
A sample of solid A is analysed by HPLC showing 72.7% of HCT 3012. Consequently the wet solid contains 6.48 g of HCT 3012 and 2.44 g of methanol by difference; yield 64.5%.
Analytical Results for Experiment 10

|  | Naproxen (%) | HCT 3013 (%) | NapOMe (%) | HCT3016 (%) | BDMN (%) | BDDN (%) |
|---|---|---|---|---|---|---|
| Starting spiked sample | 0.830 | 1.074 | 1.061 | — | 0.105 | 0.049 |
| Solid A | 0.165 | 0.246 | 0.351 | 0.016 | nd | nd |

Crystallization from CH$_3$—(CH$_2$)$_4$—CH$_3$/CH$_2$Cl$_2$/CH$_3$OH (Experiment 11)

| HCT 3012 (g) | Solvent/diluent (g) | Crystallization temperature (° C.) | Time (hours) | % Yield |
|---|---|---|---|---|
| lot # US07600379 (3.04) | CH$_3$—(CH$_2$)$_4$—CH$_3$ Lot # SA81835 (30.3) CH$_2$Cl$_2$ Lot # FL73180 (3.0) CH$_3$OH Lot # VWR08Z0365 (1.5) | −15 | 3 | 66.8 |

The products listed hereunder are charged into a three necks 100 ml glass jacketed reactor under nitrogen and under magnetical:
  hexane (30.3 g)
  methylene chloride (3.0 g)
  methanol (1.5 g)
  HCT 3012 (3.04 g).
1-2 mg of HCT 3012/01 seed (solid B) are added to the emulsion previously cooled at −15° C., the oily phase start to crystallize. The solid-liquid mixture is stirred at −15° C. for 3 hrs and then filtered through a 150 ml jacketed filter keeping the jacket at about −20° C. The cake is compressed with a pre cooled (−20° C.) stopper.
The solid material is collected into a pre cooled (−20° C.). 50 ml bottom flask and kept at −20° C.: 2.33 g of wet solid (solid A) are obtained.
A sample of solid A is analysed by HPLC showing 87.3% of HCT 3012. Consequently the wet solid contains 2.03 g of HCT 3012 and 0.3 g of solvents by difference; yield 66.8%.
Analytical Results for Experiment 11

|  | Naproxen (%) | HCT 3013 (%) | NapOMe (%) | HCT3016 (%) | BDMN (%) | BDDN (%) |
|---|---|---|---|---|---|---|
| Starting | 0.052 | 0.017 | 0.016 | 0.021 | 0.090 | nq |
| Solid A | 0.026 | 0.010 | 0.007 | 0.015 | nq | nd |

Crystallization from CH$_3$—(CH$_2$)$_4$—CH$_3$/CH$_2$Cl$_2$ (Experiment 13)

| HCT 3012 (g) | Solvent/diluent (g) | Crystallization temperature (° C.) | Time (hours) | % Yield |
|---|---|---|---|---|
| lot # US07600379 (3.043) | CH$_3$—(CH$_2$)$_4$—CH$_3$ Lot # SA81835 (30.0) CH$_2$Cl$_2$ Lot # FL73180 (3.0) | −15 | 15 | 77.2 |

The products listed hereunder are charged into a three necks 100 ml glass jacketed reactor under nitrogen and under magnetical:
  hexane (30.0 g)
  methylene chloride (3.0 g)
  HCT 3012 (3.03 g).

1-2 mg of HCT 3012/01 seed (solid B) are added to the emulsion previously cooled at −15° C. The mixture is stirred at −15° C. for 15 hrs and then filtered through a 150 ml jacketed filter keeping the jacket at about −20° C. The cake is compressed with a pre cooled (−20° C.) stopper.

The solid material is collected into a pre cooled (−20° C.) 50 ml bottom flask and kept at −20° C.: 2.34 g of wet solid (solid A) are obtained.

A sample of solid A is analysed by HPLC showing 100.4% of HCT 3012. Consequently the wet solid contains 2.34 g of HCT 3012 and no solvents; yield 77.2%.

Analytical Results for Experiment 13

|  | Naproxen (%) | HCT 3013 (%) | NapOMe (%) | HCT3016 (%) | BDMN (%) | BDDN (%) |
|---|---|---|---|---|---|---|
| Starting | 0.052 | 0.017 | 0.016 | 0.021 | 0.090 | nq |
| Solid A | 0.035 | 0.015 | 0.006 | 0.016 | nq | nq |

Experiment 14 Crystallization of HCT3012 from n-Hexane/ $CH_2Cl_2$.

| Substrate | Solvent | Crystallization T | Time | Yield |
|---|---|---|---|---|
| HCT 3012 lot # US07600379 (3.07 g) | $CH_3(CH_2)_4CH_3$ (61.53 g) $CH_2Cl_2$ (7.06 g) | −13° C. | 18 hours | 99.8% |

HCT 3012 (U.S. Pat. No. 7,600,379; 3.07 g) and $CH_2Cl_2$ (FK 73180, 3.02 g) are charged at room temperature into a three necks glass jacketed reactor (100 ml) under nitrogen and under magnetic stirring. N-Hexane (SA 81835, 4.15 g) is added gradually until the solution become cloudy. Then $CH_2Cl_2$ (7.06 g) and n-hexane (9.23 g) are alternatively added at 0° C. to maintain the turbidity. The mixture is kept under stirring to −1° C. and HCT 3012/01 crystallization seeds (about 1-2 mg) are added. Then the temperature is kept to −13° C., no crystals are formed. The mixture is heated to 20° C. and other n-hexane (52.3 g) is added to obtain an opalescent solution. Then the system is cooled down to 13° C. with an ice/salt bath and other HCT 3012/01 crystallization seeds (about 1-2 mg) are added. After few minutes the mixture starts to crystallize; the temperature is maintained at −13° C. for 2 hours, then is cooled down to −20° C. The stirring is continued for 15 hours, then is filtered through a jacketed filter (150 ml) keeping the jacket at about −20° C.

The wet solid material is kept at −20° C. in a pre cooled vial (3.05 g) (Sample A).

The mother liquors are concentrated under vacuum at about 37° C. (bath temperature) to provide an oily residue (0.12 g) (Sample B).

Analytical Results

| Entry | Naproxen (%) | HCT 3013 (%) | NapOMe (%) | HCT3016 (%) | BDMN (%) | BDDN (%) |
|---|---|---|---|---|---|---|
| Starting HCT 3012 | 0.060 | 0.017 | 0.017 | 0.004 | 0.117 | 0.051 |
| Sample A | 0.052 | 0.018 | 0.006 | 0.000 | <LOQ | <LOQ |
| Sample B | 0.052 | 0.010 | 0.118 | 0.000 | 0.904 | 0.484 |

Experiment 15 Crystallization of Neat ECT3012.

| Substrate | Solvent | Crystallization T | Time | Yield |
|---|---|---|---|---|
| HCT 3012 lot # US07600379 (3.54 g) | — | −15° C. | — | — |

HCT 3012 (U.S. Pat. No. 7,600,379; 3.54 g) is charged at room temperature into a vial under magnetic stirring. The oil is cooled to −15° C. with an ice/salt bath; the magnetic stirring stopped. HCT 3012/01 crystallization seeds (about 1-2 mg) are added and after a few minutes the oil starts to crystallize. The vial is stored at −20° C. Powder XRD pattern is perfectly comparable to is the one reported in table no. 1 of experimental section for HCT 3012 prepared in example 49. DSC analysis, carried out as reported in the experimental section, has shown the onset at 13.10° C.

Analytical Results

No data available

Experiment 16 Crystallization of HCT3012 from $CH_3OH$ (1/2 v/v).

| Substrate | Solvent | Crystallization T | Time | Yield |
|---|---|---|---|---|
| HCT 3012 lot # US07600379 (10.05 g) | $CH_3OH$ VWR 08Z3065 (20.48 g) | −15° C. | 2 hours | 86.7% |

HCT 3012 (10.05 g) is charged at room temperature into a three necks glass jacketed reactor (100 ml) under nitrogen and under magnetic stirring. The system is cooled down to −15° C. and HCT 3012/01 crystallization seeds (about 1-2 mg) are added. After 1 hour, $CH_3OH$ (20.48 g) is added. The stirring is continued for hours, then the mixture is filtered through a jacketed filter (150 ml) keeping the jacket at about −20° C.

The wet solid is dissolved in dichloromethane (50 g) and concentrated under vacuum at about +37° C. (bath temperature) to provide an oily residue (8.55 g) (Sample A).

The mother liquors are concentrated under vacuum at about +37° C. (bath temperature) to provide an oily residue (0.90 g) (Sample B).

Analytical Results

| Entry | Naproxen (%) | HCT 3013 (%) | NapOMe (%) | HCT3016 (%) | BDMN (%) | BDDN (%) |
|---|---|---|---|---|---|---|
| Starting HCT 3012 | 0.060 | 0.017 | 0.017 | 0.004 | 0.117 | 0.051 |
| Sample A | 0.047 | 0.016 | 0.016 | 0.000 | 0.087 | 0.077 |
| Sample B | 0.081 | 0.026 | 0.026 | 0.000 | 0.305 | 0.178 |

Experiment 17 Crystallization from $CH_3OH$

| Substrate | Solvent | Crystallization T | Time | Yield |
|---|---|---|---|---|
| HCT 3012 lot # US07600379 (10.13 g) | $CH_3OH$ VWR 08Z4366 (20.55 g) | −15° C. | 3 hours | 87.5% |

HCT 3012 (10.13 g) is charged into a three necks glass jacketed reactor (100 ml) under nitrogen and under magnetic stirring. The mixture is kept under stirring at −15° C. and HCT 3012/01 crystallization seeds (about 1-2 mg) are added. After 1 hour the mixture is heated to +15° C. and methanol (20.55 g) is added. Then the system is cooled down to −15° C., other HCT 3012/01 crystallization seeds (about 1-2 mg) are added and the mixture is kept under stirring for 2 hours; then is filtered through a jacketed filter (150 ml) keeping the jacket at about −20° C. and the cake is washed with pre cooled (−20° C.) methanol (10 g).

The wet solid material is dissolved in dichloromethane (50 g) and concentrated under vacuum at about +37° C. (bath temperature) to provide an oily residue (8.73 g) (Sample A).

The mother liquors are concentrated under vacuum at about +37° C. (bath temperature) to provide an oily residue (1.37 g) (Sample B).
Analytical Results

| Entry | Naproxen (%) | HCT 3013 (%) | NapOMe (%) | HCT3016 (%) | BDMN (%) | BDDN (%) |
|---|---|---|---|---|---|---|
| Starting HCT 3012 | 0.060 | 0.017 | 0.017 | 0.004 | 0.117 | 0.051 |
| Sample A | 0.021 | 0.008 | 0.013 | 0.003 | <LOQ | <LOQ |
| Sample B | 0.144 | 0.075 | 0.057 | 0.003 | 0.809 | 0.310 |

Experiment 18 Crystallization of HCT3012 from CH$_3$(CH$_2$)$_3$OH (1/10 v/v).

| Substrate | Solvent | Crystallization T | Time | Yield |
|---|---|---|---|---|
| HCT 3012 lot # US07600379 (10.18 g) | CH$_3$(CH$_2$)$_3$OH RH 63350 (100.19 g) | −15° C. | 15 hours | — |

HCT 3012 (10.18 g) is charged at room temperature into a three necks glass jacketed reactor (250 ml) under nitrogen and under mechanical stirring. 1-Butanol (100.19 g) is added and after 20 minutes a solution is formed. The temperature of system is cooled down to 15° C. and the solution become cloudy. At −5° C. oily drops start to form. HCT 3012/01 crystallization seeds (about 1-2 mg) are added and after few minutes crystals are formed. The system is cooled down to −15° C. and stirring is continued for 15 hours, then is filtered through a jacketed filter (150 ml) keeping the jacket at about −20° C. The cake is washed with pre cooled (−20° C.) 1-butanol (20 g) and the wet solid is compressed with a pre cooled (−20° C.) stopper.

The wet solid is dissolved in dichloromethane (50 g) and concentrated under vacuum at about +37° C. (bath temperature) to provide an oily residue (Sample A).

The mother liquors are concentrated under vacuum at about +37° C. (bath temperature) to provide an oily residue (Sample B).
Analytical Results

| Entry | Naproxen (%) | HCT 3013 (%) | NapOMe (%) | HCT3016 (%) | BDMN (%) | BDDN (%) |
|---|---|---|---|---|---|---|
| Starting HCT 3012 | 0.060 | 0.017 | 0.017 | 0.004 | 0.117 | 0.051 |
| Sample A | 0.013 | 0.004 | 0.008 | 0.000 | <LOQ | <LOQ |
| Sample B | 0.160 | 0.116 | 0.079 | 0.000 | 0.838 | 0.357 |

Experiment 19 Crystallization from CH$_3$OH

| Substrate | Solvent | Crystallization T | Time | Yield |
|---|---|---|---|---|
| HCT 3012 lot # US07600379 (10.28 g) | CH$_3$OH VWR 08Z4366 (20.37 g) | −15 to −5° C. | 3 hours | 88.0% |

The experiment is carried out as per Exp. No 17 keeping the temperature of the system to −5° C. when the crystallization starts.

Sample A and sample B are as per Example 17
Analytical results

| Entry | Naproxen (%) | HCT 3013 (%) | NapOMe (% | HCT3016 (%) | BDMN (%) | BDDN (%) |
|---|---|---|---|---|---|---|
| Starting HCT 3012 | 0.060 | 0.017 | 0.017 | 0.004 | 0.117 | 0.051 |
| Sample A | 0.021 | 0.008 | 0.012 | 0.003 | <LOQ | <LOQ |
| Sample B | 0.139 | 0.076 | 0.052 | 0.007 | 0.784 | 0.316 |

Experiment 20 Crystallization of HCT3012/09 from Water.

| Substrate | Solvent | Crystallization T | Time | Yield |
|---|---|---|---|---|
| HCT 3012/09 (3.15 g) | H$_2$O (purified by TL) (35.46 g) | −15° C. | 15 hours | — |

HCT 3012 (U.S. Pat. No. 7,600,379; 10.18 g) is charged at room temperature into a three necks glass jacketed reactor (100 ml) under nitrogen and under magnetic stirring. The temperature of system is cooled down to 3° C. and cooled (−20° C.). HCT3012/09 crystals (3.15 g) are added. The stirring is continued for 3 hours, then is filtered through a jacketed filter (150 ml) keeping the jacket at about 3° C.

The wet solid is kept into a vial at −20° C. (3.37 g) (Sample A).
Analytical Results No data available Experiment 21 Crystallization from CH$_3$OH

| Substrate | Solvent | Crystallization T | Time | Yield |
|---|---|---|---|---|
| HCT 3012 lot # US07600379 (10.06 g) | CH$_3$OH VWR 08Z4366 (20.11 g) | 3° C. | 15 hours | 71.9% |

Methanol (20.11 g) is charged into a three necks glass jacketed reactor (100 ml) under nitrogen and mechanical stirring. The system is kept under stirring at +20° C. HCT 3012 (10.06 g) is added and the mixture is kept under stirring for 30 minutes. Then the mixture is cooled down to +10° C. and HCT 3012/01 crystallization seeds (about 1-2 mg) are added. After about 15 minutes no solid is observed. The temperature is cooled down gradually to +8° C., +6° C. and 4° C., no solid is observed. Crystallization starts when the temperature is cooled down to +2° C.

Then the mixture is heated at +3° C. and is stirred for 15 hours; then is filtered through a jacketed filter (150 ml) keeping the jacket at about −20° C. and the cake is washed with pre cooled (−20° C.) methanol (10 g).

The wet solid material is dissolved in dichloromethane (50 g) and concentrated under vacuum at about +37° C. (bath temperature) to provide an oily residue (7.25 g) (Sample A).

The mother liquors are concentrated under vacuum at about +37° C. (bath temperature) to provide an oily residue (2.32 g) (Sample B).

Analytical Results

| Entry | Naproxen (%) | HCT 3013 (%) | NapOMe (%) | HCT3016 (%) | BDMN (%) | BDDN (%) |
|---|---|---|---|---|---|---|
| Starting HCT 3012 | 0.060 | 0.017 | 0.017 | 0.004 | 0.117 | 0.051 |
| Sample A | 0.011 | 0.003 | 0.007 | 0.001 | <LOQ | <LOQ |
| Sample B | 0.261 | 0.060 | 0.055 | 0.014 | 0.494 | 0.212 |

Experiment 22 Crystallization from $CH_3OH$

| Substrate | Solvent | Crystallization T | Time | Yield |
|---|---|---|---|---|
| HCT 3012 lot # US07600379 (10.09 g) | $CH_3OH$ VWR 08Z4366 (100.11 g) | −15° C. | 15 hours | 50.6% |

HCT 3012 (10.09 g) is charged, at room temperature, into a three necks glass jacketed reactor (250 ml) under nitrogen and under mechanical stirring. Then the oil is cooled down to −15° C. and cooled (−15° C.) methanol (100.11 g) is added. The solution is kept under stirring at −15° C. for 30 minutes. Then HCT 3012/01 crystallization seeds (about 1-2 mg) are added. The mixture is stirred for 15 hours; then is filtered through a jacketed filter (150 ml) keeping the jacket at about 0° C. and the cake is washed with pre cooled (0° C.) methanol (10 g).

The wet solid material is dissolved in dichloromethane (50 g) and concentrated under vacuum at about +37° C. (bath temperature) to provide an oily residue (5.18 g) (Sample A).

The mother liquors are concentrated under vacuum at about +37° C. (bath temperature) to provide an oily residue (4.65 g) (Sample B).

Analytical Results

| Entry | Naproxen (%) | HCT 3013 (%) | NapOMe (%) | HCT3016 (%) | BDMN (%) | BDDN (%) |
|---|---|---|---|---|---|---|
| Starting HCT 3012 | 0.060 | 0.017 | 0.017 | 0.004 | 0.117 | 0.051 |
| Sample A | 0.068 | 0.015 | 0.016 | 0.004 | 0.067 | <LOQ |
| Sample B | 0.083 | 0.018 | 0.022 | 0.005 | 0.173 | 0.064 |

Experiment 23 Crystallization of HCT 3012, Spiked with 2% of NAP, from $CH_3OH$

| Substrate | Solvent | Crystallization T | Time | Yield |
|---|---|---|---|---|
| HCT 3012 lot # US07600379 (9.82 g) NAP lot #1328040 (0.199 g = 2.0%) | $CH_3OH$ VWR 08Z4366 (100.26 g) | −40° C. | 15 hours | 63.5% |

Charge, at room temperature, under nitrogen and under mechanical stirring, into a three necks 250 ml glass jacketed to reactor in the given order:
$CH_3OH$ (100.26 g)
HCT 3012 (9.82 g)
Naproxen (0.199 g).

The homogeneous mixture is cooled to −3° C., then, after 30 minutes, HCT 3012/01 crystallization seeds (about 1-2 mg) are added. The temperature is gradually (10° C./hour) cooled down until −40° C. The stirring is continued for 15 hours at these conditions, then the crystals are filtered through a jacketed filter (150 ml) keeping the jacket at about −20° C. The cake is washed with pre cooled (−20° C.) MeOH (10 g) and the wet solid is compressed with a pre cooled (−20° C.) stopper.

The wet solid is dissolved in dichloromethane (50 g), and concentrated under vacuum at about +37° C. (bath temperature) to provide an oily residue (6.40 g) (Sample A).

The mother liquors are concentrated under vacuum at about +37° C. (bath temperature) to provide an oily residue (3.26 g) (Sample B).

Analytical Results

| Entry | Naproxen (%) | HCT 3013 (%) | NapOMe (%) | HCT3016 (%) | BDMN (%) | BDDN (%) |
|---|---|---|---|---|---|---|
| Starting HCT 3012[1] | 2.060 | 0.017 | 0.017 | 0.004 | 0.117 | 0.051 |
| Sample A | 0.444 | 0.004 | 0.007 | 0.002 | <LOQ | <LOQ |
| Sample B | 5.464 | 0.039 | 0.042 | 0.004 | 0.364 | 0.152 |

NOTE
[1] initial purity 97.0%

Experiment 25 Crystallization from Formamide at 2° C.

| Substrate | Solvent | Crystallization T | Time | Yield |
|---|---|---|---|---|
| HCT3012 lot # US07600379 (10.16 g) | $HCONH_2$ (VWR RH32530 (40.29 g) | 2° C. | 15 hours | — |

HCT 3012 (10.16 g) and formamide (20.11 g) are charged into a three necks glass jacketed reactor (100 ml) under nitrogen and under magnetic stirring. The solution is kept under stirring at +15° C. for 30 minutes, then is cooled down to 0° C. and HCT 3012/01 crystallization seeds (about 1-2 mg) are added. After about 15 minutes crystallization starts, but magnetic stirring is stopped. Then other formamide (20.18 g) is added to aid magnetic stirring. The system is cooled up to +2° C. and stirred for 15 hours; then is filtered through a jacketed filter (150 ml) keeping the jacket at about 0° C. and the cake is washed with pre cooled (0° C.) formamide (20 g).

The wet solid material is dissolved in dichloromethane (50 g) and concentrated under vacuum at about +37° C. (bath temperature) to provide an oily residue (12.62 g) which is mainly contaminated by formamide (Sample A).

Analytical Results

| Entry | Naproxen (%) | HCT 3013 (%) | NapOMe (%) | HCT3016 (%) | BDMN (%) | BDDN (%) |
|---|---|---|---|---|---|---|
| Starting HCT 3012 | 0.060 | 0.017 | 0.017 | 0.004 | 0.117 | 0.051 |
| Sample A | 0.012 | 0.011 | 0.015 | 0.003 | <LOQ | <LOQ |

3.1.2.13. Experiment 26 Crystallization from Toluene/n-Hexane.

| Substrate | Solvent | Crystallization T | Time | Yield |
|---|---|---|---|---|
| HCT 3012 lot # US07600379 (10.13 g) | $C_6H_5CH_3$ RH 60750 (20.49 g) $CH_3(CH_2)_4CH_3$ SA81835 (30.00 g) | −15° C. | 15 hours | 48.4% |

HCT 3012 (10.13 g) and toluene (20.49 g) are charged into a three necks glass jacketed reactor (100 ml) under nitrogen and under magnetic stirring. The solution is kept under stirring at +15° C. for 30 minutes. Then the system is cooled down to 0° C. and HCT 3012/01 crystallization seeds (about 1-2 mg) are added. No solid is observed. The system is cooled down to −15° C. and other HCT 3012/01 crystallization seeds (about 1-2 mg) are added. No solid is observed. The system is cooled down to −25° C. and other HCT 3012/01 crystallization seeds (about 1-2 mg) are added. No solid is observed. The system is cooled up to 0° C. and n-hexane (30 g) and other HCT 3012/01 crystallization seeds (about 1-2 mg) are added. No solid is observed. Finally the system is cooled down to −15° C. and other HCT 3012/01 crystallization seeds (about 1-2 mg) are added. After few minutes crystallization starts.

The mixture is stirred for 15 hours and then filtered through a jacketed filter (150 ml) keeping the jacket at about −15° C. The cake is washed with pre cooled (−15° C.) mixture toluene/n-hexane (25 g, 10/15 v/v).

The wet solid material is dissolved in dichloromethane (50 g), and concentrated under vacuum at about +37° C. (bath temperature) to provide an oily residue (4.98 g) (Sample A).

The mother liquors are concentrated under vacuum at about +37° C. (bath temperature) to provide an oily residue (5.41 g) (Sample B).

Analytical Results

| Entry | Naproxen (%) | HCT 3013 (%) | NapOMe (%) | HCT3016 (%) | BDMN (%) | BDDN (%) |
|---|---|---|---|---|---|---|
| Starting HCT 3012 | 0.060 | 0.017 | 0.016 | 0.004 | 0.117 | 0.051 |
| Sample A | 0.050 | 0.018 | 0.007 | 0.002 | <LOQ | <LOQ |
| Sample B | 0.093 | 0.014 | 0.025 | 0.004 | 0.218 | 0.089 |

Experiment 28 Crystallization from Diethylene Glycol at 3° C.

| Substrate | Solvent | Crystallization T | Time | Yield |
|---|---|---|---|---|
| HCT 3012 lot # US07600379 (10.05 g) | $(HOCH_2CH_2)_2O$ FK 428477/1 (20.03 g) | 3° C. | 15 hours | — |

HCT 3012 (10.05 g) and Diethylene glycol (20.03 g) are charged into a three necks glass jacketed reactor (100 ml) under nitrogen and under magnetic stirring. The mixture is kept under stirring at +15° C. for 30 minutes. Then the mixture is cooled down to 0° C. and HCT 3012/01 crystallization seeds (about 1-2 mg) is added. After about 15 minutes crystallization starts. The mixture is cooled up to +3° C. and stirred for 15 hours and then filtered through a jacketed filter (150 ml) keeping the jacket at about 0° C. The cake is washed with pre cooled (0° C.). Diethylene glycol (15 g).

The wet solid material is dissolved in dichloromethane (50 g), and concentrated under vacuum at about +37° C. (bath temperature) to provide an oily residue (11.52 g)) witch is mainly contaminated by diethylene glycol (Sample A).

Analytical Results

| Entry | Naproxen (%) | HCT 3013 (%) | NapOMe (%) | HCT3016 (%) | BDMN (%) | BDDN (%) |
|---|---|---|---|---|---|---|
| Starting HCT 3012 | 0.060 | 0.017 | 0.017 | 0.004 | 0.117 | 0.051 |
| Sample A | 0.019 | 0.006 | 0.012 | 0.004 | <LOQ | <LOQ |

Experiment 33 Crystallization of HCT 3012 Spiked with HCT 3013 from $CH_3OH$ at −10° C.

| Substrate | Solvent | Crystallization T | Time | Yield |
|---|---|---|---|---|
| lot # US07600379 (10.08 g) HCT 3013 lot # 13567-2 (0.060 g = 0.60%) | $CH_3OH$ VWR 08Z4366 (31.60 g) $CH_3COCH_3$ VWR 08H060528 (2.60 g) | −10° C. | 15 hours | 49.8% |

To a solution of HCT 3013 (13567-2; 0.060 g) in acetone (2.60 g) at room temperature, under nitrogen and magnetic stirring, is added HCT 3012 (10.08 g). The obtained solution is added in 30 minutes into a three necks glass jacketed reactor (100 ml) containing methanol (31.60 g) cooled at −10° C.

The heterogeneous mixture is kept under stirring at −10° C. for 1 hour, no crystals are formed. The mixture is stirred at −10° C. for additional 14 hrs and then filtered through a jacketed filter (50 ml) keeping the jacket at about −20° C. The cake is washed with pre cooled (−20° C.) methanol (7.9 g) and the wet solid is compressed with a pre cooled (−20° C.) stopper.

The wet solid material is dissolved in dichloromethane (50 g), and the solution is concentrated under vacuum at about +37° C. (bath temperature) to provide an oily residue (4.98 g) (Sample A).

The methanol mother liquors are concentrated under vacuum at about +37° C. (bath temperature) to provide an oily residue (4.72 g) (Sample B).

Analytical Results

| Entry | Naproxen (%) | HCT 3013 (%) | NapOMe (%) | HCT3016 (%) | BDMN (%) | BDDN (%) |
|---|---|---|---|---|---|---|
| Starting HCT 3012[2,3] | 0.060 | 0.617 | 0.017 | 0.004 | 0.117 | 0.051 |
| Sample A | 0.012 | 0.125 | 0.009 | 0.003 | <LOQ | <LOQ |
| Sample B | 0.106 | 1.176 | 0.032 | 0.004 | 0.239 | 0.102 |

Experiment 34 Crystallization of HCT 3012, Spiked with HCT 3013, from $CH_3CHOHCH_3$ at $-10°$ C.

| Substrate | Solvent | Crystallization T | Time | Yield |
|---|---|---|---|---|
| lot # US07600379 (10.00 g) HCT 3013 lot # 13567-2 (0.060 g = 0.60%) | $CH_3CHOHCH_3$ VWR 08Z4366 (31.40 g) $CH_3COCH_3$ VWR 08H060528 (2.60 g) | $-10°$ C. | 63 hours | 73.6% |

To a solution of HCT 3013 (13567-2; 0.060 g) in acetone (2.60 g) at room temperature, under nitrogen and magnetic, stirring is added HCT 3012 (10.00 g). The obtained solution is added in 30 minutes into a three necks glass jacketed reactor (100 ml) containing 2-propanol (31.60 g) cooled at $-10°$ C. The heterogeneous mixture is kept under stirring at $-10°$ C. for 1 hour, no crystals are formed. The mixture is stirred at $-10°$ C. for additional 62 hrs and then filtered through a jacketed filter (50 ml) keeping the jacket at about $-20°$ C. The cake is washed with pre cooled ($-20°$ C.) 2-propanol (7.9 g) and the wet solid is compressed with a pre cooled ($-20°$ C.) stopper.

The wet solid material is dissolved in dichloromethane (50 g), and the solution is concentrated under vacuum at about $+37°$ C. (bath temperature) to provide an oily residue (6.97 g) (Sample A).

The isopropanol/acetone mother liquors are concentrated under vacuum at about $+37°$ C. (bath temperature) to provide an oily residue (2.57 g) (Sample B).

Analytical Results

| Entry | Naproxen (%) | HCT 3013 (%) | NapOMe (%) | HCT3016 (%) | BDMN (%) | BDDN (%) |
|---|---|---|---|---|---|---|
| Starting HCT 3012[2,3] | 0.060 | 0.617 | 0.017 | 0.004 | 0.117 | 0.051 |
| Sample A | 0.022 | 0.180 | 0.012 | 0.003 | <LOQ | <LOQ |
| Sample B | 0.149 | 2.257 | 0.040 | 0.005 | 0.497 | 0.163 |

Notes
1) The % of impurity was calculated on the basis of HCT3013 added and not determinate by HPLC.
[2)] Starting sample purity: 98.4%

Experiment 35 Crystallization of HCT 3012, Spiked with HCT 3016, from $CH_3CHOHCH_3$/THF at $0°$ C.

| Substrate | Solvent | Crystallization T | Time | Yield |
|---|---|---|---|---|
| lot # US07600379 (10.08 g) HCT 3016 lot # 13548-2 (0.03 g = 0.30%)) | $CH_3CHOHCH_3$ VWRK38782434 (52.36 g) THF VWRI391401743 (5.95 g) | $0°$ C. | 1 hour | 79.2% |

Charge under nitrogen and magnetic stirring, at room temperature, into a three necks 100 ml glass jacketed reactor in the given order:

2-Propanol (52.36 g)

THF (5.95 g)

HCT 3016 (0.03 g)

HCT 3012 (10.08 g).

The solution is cooled to $0°$ C. and HCT 3012/01 crystallization seeds (about 1-2 mg) are added. Crystallization starts while the mixture is stirred for 1 hour a $0°$ C. It is cooled to $-10°$ C. and the solid is filtered through a jacketed filter (150 ml) keeping the jacket at $-20°$ C. The cake is washed with pre cooled ($-20°$ C.) 2-propanol (15.7 g) and the wet solid is compressed with a pre cooled ($-20°$ C.) stopper.

The wet solid is dissolved in dichloromethane (50 g), and the solution is concentrated under vacuum at about $+37°$ C. (bath temperature) to provide an oily residue (7.79 g) (Sample A).

The mother liquors are concentrated under vacuum at about $+37°$ C. (bath temperature) to provide an oily residue (2.17 g) (Sample B).

Analytical Results

| Entry | Naproxen (%) | HCT 3013 (%) | NapOMe (%) | HCT3016 (%) | BDMN (%) | BDDN (%) |
|---|---|---|---|---|---|---|
| Starting HCT 3012[2),3] | 0.060 | 0.017 | 0.017 | 0.304 | 0.117 | 0.051 |
| Sample A | 0.017 | 0.004 | 0.008 | 0.202 | <LOQ | <LOQ |
| Sample B | 0.151 | 0.067 | 0.051 | 0.641 | 0.518 | 0.224 |

Notes
1) The % of impurity was calculated on the basis of HCT3013 added and not determined by HPLC.
[2)] Starting sample purity: 98.7%.

Experiment 36 Crystallization from $CH_3OH$

| Substrate | Solvent | Crystallization T | Time | Yield |
|---|---|---|---|---|
| HCT 3012 lot # US07600379 (30.14 g) | $CH_3OH$ VWR 08Z4366 (60.31 g) | $3°$ C. | 15 hours | 66.6% |

HCT 3012 (30.14 g) and methanol (60.31 g) are charged into a three necks glass jacketed reactor (250 ml) under nitrogen and under mechanical stirring. The mixture is kept under stirring at $+20°$ C. for 30 minutes. Then the temperature is cooled down to $+3°$ C. and after about 15 minutes HCT 3012/01 crystallization seeds (about 1-2 mg) are added. The mixture is stirred for 15 hours; then is filtered through a jacketed filter (150 ml) keeping the jacket at about $-20°$ C. and the cake is washed with pre cooled ($-20°$ C.) methanol (30 g).

A portion of wet solid (13.16 g) is transferred in a round bottom flask and cooled into an ice/salt bath, under vacuum, for 6 hours to provide a dry solid (9.65 g) (Sample A dry).

The rest of wet solid material is dissolved in dichloromethane (50 g) and concentrated under vacuum at about +37° C. (bath temperature) to provide an oily residue (11.64 g) (Sample A wet).

The mother liquors are concentrated under vacuum at about +37° C. (bath temperature) to provide an oily residue (8.54 g) (Sample B).

Analytical Results

| Entry | Naproxen (%) | HCT 3013 (%) | NapOMe (%) | HCT3016 (%) | BDMN (%) | BDDN (%) |
|---|---|---|---|---|---|---|
| Starting HCT 3012 | 0.060 | 0.017 | 0.017 | 0.004 | 0.117 | 0.051 |
| Sample A dry | 0.006 | 0.002 | 0.005 | 0.002 | <LOQ | <LOQ |
| Sample A wet | 0.009 | 0.003 | 0.006 | 0.002 | <LOQ | <LOQ |
| Sample B | 0.203 | 0.053 | 0.056 | 0.005 | 0.430 | 0.186 |

3.1.2.23. Experiment 37 Crystallization from CH₃OH/Toluene (3/1 v/v).

| Substrate | Solvent | Crystallization T | Time | Yield |
|---|---|---|---|---|
| HCT 3012 lot # US07600379 (10.21 g) | CH₃OH (15.02 g) VWR 08Z4366 C₆H₅CH₃ VWRK33730525439 (5.01 g) | −10° C. | 15 hours | 17.8% |

The products listed hereunder are charged, at room temperature, into a three necks 100 ml glass jacketed reactor under nitrogen and under magnetic stirring:
  Methanol (15.02 g)
  Toluene (5.01 g)
  HCT 3012 (10.21 g).

The solution is cooled down until +3° C. remaining clear, then is cooled down until −10° C. (the solution becomes cloudy at −5° C.) for 15 minutes. As soon as HCT 3012/01 crystallization to seeds (about 1-2 mg) are added. The mixture is stirred at this temperature for 15 hour and then filtered through a jacketed filter (150 ml) keeping the jacket at about −20° C. The cake is washed with pre cooled (−20° C.) mixture methanol/toluene (10 g, 7.5/2.5 v/v) and the wet solid is compressed with a pre cooled (−20° C.) stopper.

The wet solid material is dissolved in dichloromethane (50 g), and concentrated under vacuum at about +37° C. (bath temperature) to provide an oily residue (1.84 g) (Sample A).

The mother liquors are concentrated under vacuum at about +37° C. (bath temperature) to provide an oily residue (8.41 g) (Sample B).

Analytical Results

| Entry | Naproxen (%) | HCT 3013 (%) | NapOMe (%) | HCT 3039 (%) | BDMN (%) | BDDN (%) |
|---|---|---|---|---|---|---|
| Starting HCT 3012 | 0.060 | 0.017 | 0.017 | <LOQ | 0.117 | 0.051 |
| Sample A | 0.011 | 0.003 | 0.006 | <LOQ | <LOQ | <LOQ |
| Sample B | 0.067 | 0.018 | 0.019 | <LOQ | 0.124 | 0.059 |

Experiment 38 Crystallization from CH₃OH/n-Hexane (3/1 v/v).

| Substrate | Solvent | Crystallization T | Time | Yield |
|---|---|---|---|---|
| HCT 3012 lot # US07600379 (10.08 g) | CH₃OH VWR 08Z4366 (15.08 g) CH₃(CH₂)₄CH₃ SA81835 (5.03 g) | 0° C. | 15 hours | 66.7% |

The products listed hereunder are charged, at room temperature, into a three necks 100 ml glass jacketed reactor under nitrogen and under magnetic stirring:
  Methanol (15.08 g)
  n-Hexane (5.03 g)
  HCT 3012 (10.08 g).

The solution is cooled down until +3° C. (the solution becomes cloudy at +15° C.), then, after 15 minutes, HCT 3012/01 crystallization seeds (about 1-2 mg) are added. After 30 minutes no solid is observed. The mixture is cooled down to 0° C. and other HCT 3012/01 crystallization seeds (about 1-2 mg) are added. After 30 minutes no solid is observed. Then the mixture is cooled down to −3° C. and after few minutes crystallization starts. The temperature system is kept at 0° C., is stirred for 15 hour and then filtered through a jacketed filter (150 ml) keeping the jacket at about −20° C. The cake is washed with pre cooled (−20° C.) mixture methanol/n-hexane (10 g, 7.5/2.5 v/v) and the wet solid is compressed with a pre cooled (−20° C.) stopper. The wet solid material is dissolved in dichloromethane (50 g), and concentrated under vacuum at about +37° C. (bath temperature) to provide an oily residue (6.54 g) (Sample A). The mother liquors are concentrated under vacuum at about +37° C. (bath temperature) to provide an oily residue (3.48 g) (Sample B)

Analytical Results

| Entry | Naproxen (%) | HCT 3013 (%) | NapOMe (%) | HCT3016 (%) | BDMN (%) | BDDN (%) |
|---|---|---|---|---|---|---|
| Starting HCT 3012 | 0.060 | 0.017 | 0.017 | 0.004 | 0.117 | 0.051 |
| Sample A | 0.013 | 0.004 | 0.008 | 0.002 | <LOQ | <LOQ |
| Sample B | 0.136 | 0.040 | 0.038 | 0.004 | 0.299 | 0.137 |

Experiment 39 Crystallization of HCT 3012, spiked with 1% of NAP, from CH₃OH

| Substrate | Solvent | Crystallization T | Time | Yield |
|---|---|---|---|---|
| HCT 3012 lot # US07600379 (10.08 g) NAP lot #PM 7BB-KL (0.100 g = 1.0%) | CH₃OH VWR 08Z4366 (22.11 g) | 3° C. | 15 hours | 58.4% |

Charge, at room temperature, under nitrogen and under magnetic stirring, into a three necks 100 ml glass jacketed reactor in the given order:
  CH₃OH (22.11 g)
  HCT 3012 (10.08 g)
  Naproxen (0.100 g).

The heterogeneous mixture is cooled to 3° C., then, after 15 minutes, HCT 3012/01 crystallization seeds (about 1-2 mg) are added. After 30 minutes crystals are formed. The stirring is continued for 15 hours, then the crystals are filtered through a jacketed filter (150 ml) keeping the jacket at about −20° C. The cake is washed with pre cooled (−20° C.) MeOH (10 g) and the wet solid is compressed with a pre cooled (−20° C.) stopper. The wet solid is dissolved in dichloromethane (50 g), and concentrated under vacuum at about +37° C. (bath temperature) to provide an oily residue (6.14 g) (Sample A).

The mother liquors are concentrated under vacuum at about +37° C. (bath temperature) to provide an oily residue (3.84 g) (Sample B).

Analytical Results

| Entry | Naproxen (%) | HCT 3013 (%) | NapOMe (%) | HCT3016 (%) | BDMN (%) | BDDN (%) |
|---|---|---|---|---|---|---|
| Starting HCT 3012[1] | 1.060 | 0.017 | 0.017 | 0.004 | 0.117 | 0.051 |
| Sample A | 0.134 | 0.003 | 0.008 | 0.002 | <LOQ | <LOQ |
| Sample B | 2.119 | 0.042 | 0.054 | 0.004 | 0.323 | 0.147 |

NOTE
[1]Initial purity 98.0%

Experiment 40 Crystallization from CH₃OH at −15° C.

| Substrate | Solvent | Crystallization T | Time | Yield |
|---|---|---|---|---|
| HCT 3012 lot # US07600379 (10.09 g) | CH₃OH VWR 08Z4366 (20.02 g) | −15° C. | 15 hours | 71.6% |

HOT 3012 (10.09 g) is charged into a three necks glass jacketed reactor (100 ml) under nitrogen and under magnetic stirring. The system is kept under stirring at +20° C. for 30 minutes. Then the temperature is cooled down to −15° C. and pre-cooled methanol (20.02 g) is added. The low temperature make difficult the magnetic stirring. After few minutes crystallization starts. The mixture is stirred for 15 hours; then is filtered through a jacketed filter (150 ml) keeping the jacket at about −20° C. and the cake is washed with pre cooled (−20° C.) methanol (40 g).

The wet solid is dissolved in dichloromethane (50 g) and is concentrated under vacuum at about +37° C. (bath temperature) to provide an oily residue (7.58 g) (Sample A).

The mother liquors are concentrated under vacuum at about +37° C. (bath temperature) to provide an oily residue (2.14 g) (Sample B).

Analytical Results

| Entry | Naproxen (%) | HCT 3013 (%) | NapOMe (%) | HCT3016 (%) | BDMN (%) | BDDN (%) |
|---|---|---|---|---|---|---|
| Starting HCT 3012 | 0.060 | 0.017 | 0.017 | 0.004 | 0.117 | 0.051 |
| Sample A | 0.035 | 0.010 | 0.012 | 0.002 | <LOQ | <LOQ |
| Sample B | 0.138 | 0.036 | 0.037 | 0.004 | 0.449 | 0.210 |

Experiment 41 Crystallization from CH₃OH at −15° C.

| Substrate | Solvent | Crystallization T | Time | Yield |
|---|---|---|---|---|
| HCT 3012 lot # US07600379 (30.13 g) | CH₃OH VWR 08Z4366 (60.15 g) | −15° C. | 15 hours | 76.2% |

The experiment is carried out as per Exp. No 40 using mechanical stirring instead of magnetic stirring and seeding the crystallization.

Sample A and sample B are as per Example 40

Analytical Results

| Entry | Naproxen (%) | HCT 3013 (%) | NapOMe (%) | HCT3016 (%) | BDMN (%) | BDDN (%) |
|---|---|---|---|---|---|---|
| Starting HCT 3012 | 0.060 | 0.017 | 0.017 | 0.004 | 0.117 | 0.051 |
| Sample A | 0.028 | 0.008 | 0.014 | 0.002 | <LOQ | <LOQ |
| Sample B | 0.172 | 0.054 | 0.045 | 0.005 | 0.587 | 0.253 |

Experiment 42 Crystallization from CH₃OH from −15° C. to 3° C.

| Substrate | Solvent | Crystallization T | Time | Yield |
|---|---|---|---|---|
| HCT 3012 lot # US07600379 (30.09 g) | CH₃OH VWR 08Z4366 (60.09 g) | −15° C. to 3° C. | 15 hours | 67.7% |

HCT 3012 (30.09 g) is charged into a three necks glass jacketed reactor (250 ml) under nitrogen and under mechanical stirring. The system is cooled down to −15° C. and pre-cooled methanol (60.09 g) is added. After 5-10 minutes HCT 3012/01 crystallization seeds (about 1-2 mg) are added. When the crystallization starts, the temperature system is heated gradually to 3° C. (in 1 hour). The mixture is stirred for 15 hours; then is filtered through a jacketed filter (150 ml) keeping the jacket at about −20° C. and the cake is washed with pre cooled (−20° C.) methanol (50 g).

The wet solid is dissolved in dichloromethane (50 g) and concentrated under vacuum at about +37° C. (bath temperature) to provide an oily residue (20.98 g) (Sample A).

The mother liquors are concentrated under vacuum at about +37° C. (bath temperature) to provide an oily residue (8.19 g) (Sample B).

Analytical Results

| Entry | Naproxen (%) | HCT 3013 (%) | NapOMe (%) | HCT3016 (%) | BDMN (%) | BDDN (%) |
|---|---|---|---|---|---|---|
| HCT 3012 | 0.060 | 0.017 | 0.017 | 0.004 | 0.117 | 0.051 |
| Sample A | 0.020 | 0.006 | 0.009 | 0.005 | <LOQ | <LOQ |
| Sample B | 0.156 | 0.049 | 0.052 | 0.015 | 0.343 | 0.144 |

Experiment 43 Crystallization from $CH_3OH$ from 3° C. to 5° C.

| Substrate | Solvent | Crystallization T | Time | Yield |
|---|---|---|---|---|
| HCT 3012 lot # US07600379 (30.01 g) | $CH_3OH$ VWR 08Z4366 (60.04 g) | 3° C. to 5° C. | 15 hours | 67.3% |

HCT 3012 (30.01 g) is charged into a three necks glass jacketed reactor (250 ml) under nitrogen and under mechanical stirring.

The system is kept under stirring at +20° C. for 30 minutes. Then the temperature is cooled down to 3° C. and pre-cooled methanol (60.04 g) is added. After 10-15 minutes HCT 3012/01 crystallization seeds (about 1-2 mg) are added and in about 30 minutes crystallization starts. After 30 minutes the temperature is kept to 4° C. and no changes in the aspect of crystals are observed. Then the temperature is kept to 5° C. in about other 30 minutes but the powdery crystals becomes lumpy and starts to fuse. Then the temperature of the mixture is kept to 4° C. and is stirred for 15 hours; then is filtered through a jacketed filter (150 ml) keeping the jacket at about −20° C. and the cake is washed with pre cooled (−20° C.) methanol (50 g).

The wet solid is dissolved in dichloromethane (50 g) and concentrated under vacuum at about +37° C. (bath temperature) to provide an oily residue (19.80 g) (Sample A).

The mother liquors are concentrated under vacuum at about +37° C. (bath temperature) to provide an oily residue (10.04 g) (Sample B).

Analytical Results

| Entry | Naproxen (%) | HCT 3013 (%) | NapOMe (%) | HCT3016 (%) | BDMN (%) | BDDN (%) |
|---|---|---|---|---|---|---|
| Starting HCT 3012 | 0.060 | 0.017 | 0.017 | 0.004 | 0.117 | 0.051 |
| Sample A | 0.011 | 0.003 | 0.007 | 0.005 | <LOQ | <LOQ |
| Sample B | 0.127 | 0.043 | 0.046 | 0.006 | 0.254 | 0.085 |

Experiment 45 Crystallization from $CH_3OH$/Toluene (45/1 v/v).

| Substrate | Solvent | Crystallization T | Time | Yield |
|---|---|---|---|---|
| HCT 3012 lot # US07600379 (5.05 g) | $CH_3OH$ VWR 08Z4366 (9.80 g) $C_6H_5CH_3$ VWRK33730525439 (0.20 g) | 3° C. | 1 hour | 48.0% |

The experiment is carried out as per Exp. No 37 at +3° C. and for 1 h instead of 0° C. and 15 h.

Sample A and sample B are as per Example 37

Analytical Results

| Entry | Naproxen (%) | HCT 3013 (%) | NapOMe (%) | HCT3016 (%) | BDMN (%) | BDDN (%) |
|---|---|---|---|---|---|---|
| Starting HCT 3012 | 0.060 | 0.017 | 0.017 | 0.004 | 0.117 | 0.051 |
| Sample A | 0.020 | 0.006 | 0.011 | 0.002 | <LOQ | <LOQ |
| Sample B | 0.121 | 0.037 | 0.033 | 0.004 | 0.250 | 0.111 |

Experiment 47 Crystallization from $CH_3CHOHCH_3$/Toluene

| Substrate | Solvent | Crystallization T | Time | Yield |
|---|---|---|---|---|
| HCT 3012 lot # US07600379 (5.06 g) | $CH_3CHOHCH_3$ VWRK38782434828 (9.80 g) $C_6H_5CH_3$ VWRK33730525439 (0.20 g) | 3° C. | 3 hours | 78.9% |

The experiment is carried out as per Exp. No 45 using 2-Propanol instead of $CH_3OH$.

Sample A and sample B are as per Example 37

Analytical Results

| Entry | Naproxen (%) | HCT 3013 (%) | NapOMe (%) | HCT3016 (%) | BDMN (%) | BDDN (%) |
|---|---|---|---|---|---|---|
| Starting HCT 3012 | 0.060 | 0.017 | 0.017 | 0.004 | 0.117 | 0.051 |
| Sample A | 0.033 | 0.008 | 0.013 | 0.003 | <LOQ | <LOQ |
| Sample B | 0.206 | 0.085 | 0.048 | 0.005 | 0.801 | 0.264 |

Experiment 49 Crystallization of HCT 3012 from $CH_3OH$ (Influence of Quality and Quantity of the Seeds)

| Substrate | Solvent | Crystallization T | Time | Yield |
|---|---|---|---|---|
| HCT 3012 #Ro/2059-20 (99.92 g) | $CH_3OH$ VWR 08Z4366 (202.0 g) | 3° C. | 15 hours | 36.3% |

HCT 3012 (99.92 g) and methanol (202.0 g) are charged into a three necks glass jacketed reactor (500 ml) under nitrogen and under mechanical stirring. The system is kept under stirring at +20° C. for 30 minutes. Then the temperature is cooled to 3° C. and HCT 3012/01 crystallization seeds (about 1-2 mg) are added. After 20 minutes the mixture starts to crystallize. The stirring is continued for 15 hours, then the crystals are filtered through a jacketed filter (150 ml) keeping the jacket at about −20° C. The cake is washed with pre cooled (−20° C.) Methanol (50 g) and the wet solid is compressed with a pre cooled (−20° C.) stopper.

The wet solid is dissolved in dichloromethane (100 g) and concentrated under vacuum at about +37° C. (bath temperature) to provide an oily residue (71.5 g) witch is crystallized twice in the same manner to obtain a mixture witch is filtered through a jacketed filter (150 ml) keeping the jacket at about −20° C. and the cake is washed with pre cooled (−20° C.) methanol (30 g).

A portion of wet solid is transferred in a round bottom flask and cooled into an ice/salt bath, under vacuum, for 6 hours to provide a dry solid (19.28 g) (Sample A dry). Powder XRD pattern is perfectly comparable to the one reported in table no. 1 of experimental section for wet HCT 3012 prepared below). DSC analysis, carried out as reported in the experimental section, has shown the onset at 14.01° C.

The rest of wet solid material is collected in a pre cooled vial (16.34 g) (Sample A wet). Powder XRD pattern is the one reported in table no. 1 of experimental section. DSC analysis, carried out as reported in the experimental section, has shown the onset at 13.37° C.

The mother liquors are concentrated under vacuum at about 37° C. (bath temperature) to provide an oily residue (14.37 g) (Sample B).

Analytical Results

| Entry | Naproxen (%) | HCT 3013 (%) | NapOMe (%) | HCT3016 (%) | BDMN (%) | BDDN (%) |
|---|---|---|---|---|---|---|
| Starting HCT 3012 | <LOQ | <LOQ | 0.008 | <LOQ | <LOQ | <LOQ |
| Sample A dry | <LOQ | <LOQ | <LOQ | <LOQ | <LOQ | <LOQ |
| Sample A wet | <LOQ | <LOQ | <LOQ | <LOQ | <LOQ | <LOQ |
| Sample B | <LOQ | <LOQ | 0.003 | <LOQ | <LOQ | <LOQ |

Experiment 50 Crystallization of HCT 3012, Spiked with 10% of NAP, from $CH_3OH$.

| Substrate | Solvent | Crystallization T | Time | Yield |
|---|---|---|---|---|
| HCT 3012 lot # US07600379 (29.97 g) NAP lot # FK 1328040 (2.99 g = 10%) | $CH_3OH$ VWR 08Z4366 (61.03 g) | 3° C. | 15 hours | 56.8% |

Charge, at room temperature, under nitrogen and under magnetic stirring, into a three necks 250 ml glass jacketed reactor in the given order:
$CH_3OH$ (61.03 g)
HCT 3012 (29.97 g)
Naproxen (2.99 g).

The heterogeneous mixture is cooled to 3° C., then, after 15 minutes, HCT 3012/01 crystallization seeds (about 1-2 mg) are added. After 1 hour no crystals are formed. The temperature system is then cooled to 0° C.; no crystals are formed. Then the temperature is kept to –3° C.; no crystals are formed. Other HCT 3012/01 crystallization seeds (about 1-2 mg) are added and after 30 minutes the mixture starts to crystallize. The stirring is continued for 15 hours, then the crystals are filtered through a jacketed filter (150 ml) keeping the jacket at about –20° C. The cake is washed with pre cooled (–20° C.) Methanol (30 g) and the wet solid is compressed with a pre cooled (–20° C.) stopper.

The wet solid is dissolved in dichloromethane (40 g), and concentrated under vacuum at about +37° C. (bath temperature) to provide an oily residue (17.6 g) (Sample A).

The mother liquors are concentrated under vacuum at about +37° C. (bath temperature) to provide an oily residue (11.71 g) (Sample B).

Analytical Results

| Entry | Naproxen (%) | HCT 3013 (%) | NapOMe (%) | HCT3016 (%) | BDMN (%) | BDDN (%) |
|---|---|---|---|---|---|---|
| Starting HCT 3012[1] | 10.060 | 0.017 | 0.017 | 0.004 | 0.117 | 0.051 |
| Sample A | 1.014 | 0.003 | 0.006 | 0.002 | <LOQ | <LOQ |
| Sample B | 21.723 | 0.055 | 0.069 | 0.004 | 0.396 | 0.178 |

NOTE
[1]Initial purity 89.0%

Experiment 51 Crystallization of HCT 3012, Spiked with 0.5% of Different Impurities, from $CH_3OH$.

| Substrate | Solvent | Crystallization T | Time | Yield |
|---|---|---|---|---|
| HCT 3012 #Ro/2059-20 (10.06 g) HCT 3013 #SOL 13567-2 (0.051 g = 0.5%) HCT 3016 #SOL 13548-2 (0.050 g = 0.5%) NapOMe #SOL 13560-2 (0.050 g = 0.5%) NAP #PM 7BB-KL (0.051 g = 0.5%) | $CH_3OH$ VWR 08Z4366 (102.94 g) | –3° C. | 30 hours | 19.0% |

Charge, at room temperature, under nitrogen and under magnetic stirring, into a three necks 250 ml glass jacketed reactor in the given order:
$CH_3OH$ VWR 08Z4366 (102.94 g)
HCT 3012 (10.06 g)
HCT 3013 (0.051 g)
HCT 3016 (0.050 g)
NapOMe (0.050 g)
Naproxen (0.051 g).

The solution is cooled to 3° C., then, after 15 minutes, HCT 3012/49 crystallization seeds (about 300 mg) are added. After 2 hours no crystals are formed. The temperature is kept to 0° C.; no crystals are formed. The stirring is continued for 15 hours, then the temperature is kept to –3° C. and after 20 minutes the crystallization starts. The stirring is continued for 15 hours, the crystals are filtered through a jacketed filter (150 ml) keeping the jacket at about –20° C. The cake is washed with pre cooled (–20° C.) MeOH (20 g) and the wet solid is compressed with a pre cooled (–20° C.) stopper.

The wet solid is dissolved in dichloromethane (20 g) and concentrated under vacuum at about +37° C. (bath temperature) to provide an oily residue (1.96 g) (Sample A).

The mother liquors are concentrated under vacuum at about +37° C. (bath temperature) to provide an oily residue (8.87 g) (Sample B).

Analytical Results

| Entry | Naproxen (%) | HCT 3013 (%) | NapOMe (%) | HCT3016 (%) | BDMN (%) | BDDN (%) |
|---|---|---|---|---|---|---|
| Starting HCT 3012[1] | 0.501 | 0.501 | 0.508 | 0.501 | <LOQ | <LOQ |
| Sample A | 0.032 | 0.042 | 0.086 | 0.177 | <LOQ | <LOQ |
| Sample B | 0.447 | 0.540 | 0.539 | 0.477 | <LOQ | <LOQ |

NOTE
[1]Initial purity 96.8%

Experiment 52 Crystallization of HCT 3012 from CH$_3$OH.

| Substrate | Solvent | Crystallization T | Time | Yield |
|---|---|---|---|---|
| HCT 3012 #Ro/2059-20 (10.35 g) | CH$_3$OH VWR 08Z4366 (103.20 g) | −3° C. | 15 hours | 13.3% |
| HCT 3013 #SOL 13567-2 (0.052 g = 0.5%) | | | | |
| HCT 3016 #SOL 13548-2 (0.050 g = 0.5%) | | | | |
| NapOMe #SOL 13560-2 (0.052 g = 0.5%) | | | | |
| NAP #PM 7BB-KL (0.050 g = 0.5%) | | | | |

The experiment is carried out as per Exp. No 51 using 0.010 g of HCT 3012/49 instead of 0.300 g.

Analytical Results

| Entry | Naproxen (%) | HCT 3013 (%) | NapOMe (%) | HCT3016 (%) | BDMN (%) | BDDN (%) |
|---|---|---|---|---|---|---|
| Starting HCT 3012 | 0.501 | 0.501 | 0.508 | 0.501 | <LOQ | <LOQ |
| Sample A | 0.036 | 0.053 | 0.102 | 0.218 | <LOQ | <LOQ |
| Sample B | 0.414 | 0.528 | 0.534 | 0.458 | <LOQ | <LOQ |

Powder XRD Analysis of HCT 3012 Samples of Examples 05, 06, 15 and 49.

Powder XRD analysis of HCT 3012 samples were performed by using Cu K$_\alpha$ radiation with a Thermo X'tra powder XRD diffractometer operating in θ-θ geometry, equipped with a Si(Li) Thermo Electron solid state detector and a non-environmental Anton Paar TTK450 chamber operating in the temperature range 81-723K. The X-ray tube voltage and amperage were set to 42.5 KW and 40 mA. The analyses were performed at 273K, keeping constant the chamber temperature for the whole analysis. The specimens were prepared directly in the freezer used to stock the samples and transported to the operating chamber in an ice bath. The XRD patterns were collected by using a divergent optics in parafocusing Bragg-Brentano geometry in the range 2θ=3-40°, with 0.05° steps and 2 sec/step counting times. The divergence and scatter slits were set at 2 and 3 mm, respectively, whereas the detector scatter and reference slits were set at 0.5 and 0.2 mm, respectively.

Data were collected and analysed using the Win XRD w2.0-5 software. XRD patterns were indexed with TREOR 90.

Results

The powder XRD patterns of all the analysed samples are perfectly comparable, indicating the presence of the same crystal phase in all the samples, independently from the solvent used in the crystallization process and from wet or dry indications. Only small variations of the relative intensity, consistent with different degree of preferential orientation, produced in the sample preparation, were observed in the experimental patterns, whereas the peak positions were found to be reproducible within the experimental errors. As example, the pattern recorded for wet sample 49 is tabulated in table no. 1.

TABLE NO. 1 tabulated XRD pattern for HCT 3012 sample A methanol wet

| 2θ (°) | D (Å) | Rel intensity |
|---|---|---|
| 5.62 | 15.712 | 7 |
| 9.82 | 9.002 | 5 |
| 10.12 | 8.733 | 10 |
| 11.13 | 7.944 | 23 |
| 12.32 | 7.177 | 2 |
| 13.05 | 6.779 | 22 |
| 15.76 | 5.618 | 8 |
| 16.43 | 5.391 | 21 |
| 16.69 | 5.307 | 10 |
| 17.33 | 5.112 | 17 |
| 17.88 | 4.954 | 66 |
| 18.47 | 4.799 | 31 |
| 19.19 | 4.622 | 26 |
| 19.70 | 4.503 | 73 |
| 20.27 | 4.378 | 37 |
| 21.26 | 4.177 | 47 |
| 22.13 | 4.014 | 100 |
| 22.30 | 3.984 | 97 |
| 22.73 | 3.908 | 56 |
| 24.24 | 3.668 | 42 |
| 24.66 | 3.607 | 11 |
| 25.13 | 3.540 | 17 |
| 25.91 | 3.436 | 18 |
| 26.24 | 3.393 | 13 |
| 26.75 | 3.330 | 7 |
| 27.20 | 3.276 | 46 |
| 27.45 | 3.247 | 9 |
| 27.95 | 3.190 | 3 |
| 28.68 | 3.110 | 2 |
| 28.90 | 3.087 | 10 |
| 29.65 | 3.010 | 5 |
| 30.22 | 2.955 | 9 |
| 31.45 | 2.842 | 5 |
| 31.73 | 2.818 | 8 |
| 32.27 | 2.772 | 7 |
| 32.92 | 2.719 | 3 |
| 33.17 | 2.699 | 5 |
| 33.90 | 2.642 | 8 |
| 34.12 | 2.626 | 10 |
| 34.95 | 2.565 | 4 |
| 35.05 | 2.558 | 5 |
| 35.56 | 2.522 | 2 |
| 36.22 | 2.478 | 6 |
| 36.47 | 2.462 | 6 |
| 36.97 | 2.429 | 3 |
| 37.35 | 2.406 | 3 |
| 38.18 | 2.355 | 5 |
| 38.44 | 2.340 | 3 |
| 38.89 | 2.314 | 3 |
| 39.11 | 2.302 | 4 |
| 39.64 | 2.272 | 2 |

DSC Analysis of HCT 3012 Samples of Examples 05, 15 and 49

Differential Scanning Calorimetry analyses were carried out with the instrument DSC 821$^e$ (Mettler-Toledo) with intracooler, under the following conditions:

Temperature ramp: −30/+25° C. (ISO 10 min at −30° C.; ramp to +25° C. at 2° C./min)

Heating rate: 2° C./min

Gas: nitrogen

Flow: 30 mL/min

Sample Holder Hermetically closed Aluminium pan

Evaluation software: Stare SW 9.20

All the samples were stored at −30° C. and put into the instrument set at −30° C.

SUMMARY TABLE 5[1)]
Crystallization experiments in $CH_3OH$ (HCT 3012/$CH_3OH$ = 1/10 w/w)

| Experiments | Temp. | Time[2)] | Yield[3)] (Scale) | Naproxen (%) | HCT 3013 (%) | NapOMe (%) | HCT 3016 (%) | BDMN (%) | BDDN (%) | Notes |
|---|---|---|---|---|---|---|---|---|---|---|
| LOQ concentration (%) | | | | 0.003 | 0.003 | 0.003 | 0.003 | 0.05 | 0.05 | |
| HCT3012 #US07600379 | — | — | | 0.052 | 0.017 | 0.016 | 0.021 | 0.090 | nq | Starting HCT3012 |
| 01 | −15° C. | 3 h | — (5 g) | 0.006 | 0.004 | 0.015 | 0.014 | nd | nd | Seeds preparation |
| 02 | −15° C. | 3 h | 54.1% (5 g) | 0.016 | 0.006 | 0.008 | 0.016 | nd | nd | No seeding |
| 03 | −5° C. | 3 h | 42.2% (12 g) | 0.012 | 0.004 | 0.006 | 0.012 | nd | nd | |
| 04 | −15° C. | 15 h | 66.5% (20 g) | 0.012 | 0.004 | 0.007 | 0.011 | nd | nd | |
| 07 | −25° C. | 15 h | 82.1% (10 g) | 0.013 | 0.005 | 0.007 | 0.017 | nd | nd | |
| 09 | −15° C. | 15 h | 75.3% (20 g) | 0.008 | 0.003 | 0.006 | 0.015 | nd | nd | |
| 12 | −15° C. | 15 h | 66.2% (20 g) | 0.014 | 0.005 | 0.007 | 0.017 | nd | nd | |
| 08 fluffy crystals | −15° C. | 15 h | 62.1% (10 g) | 0.011 | 0.005 | 0.009 | 0.017 | nd | nd | Methanol/ Water 95/5 |
| 08 hard solid | | | 15.5% (10 g) Total yield 77.6% | 0.007 | nq | 0.009 | 0.019 | nd | nq | |
| 10 Spiked batch | | — | — | 0.830 | 1.074 | 1.061 | — | 0.105 | 0.049 | |
| 10 | −15° C. | 15 h | 64.5% (10 g) | 0.165 | 0.246 | 0.351 | 0.016 | nd | nd | |

Notes to table:
[1)]all data listed in the table refer to the isolated wet crystals;
[2)]permanence time at the temperature of choice prior to isolation of wet crystals;
[3)]yields listed in the table refer to the content of HCT3012 in the isolated wet crystals;

SUMMARY TABLE 6[1)]
Crystallization experiments in alcohol (HCT 3012/alcohol = 1/10 w/w)

| Experiments | Temp. | Time[2)] | Yield[3)] Scale | Naproxen (%) | HCT3013 (%) | NapOMe (%) | HCT3016 (%) | BDMN (%) | BDDN (%) | Notes |
|---|---|---|---|---|---|---|---|---|---|---|
| | | | | 0.052 | 0.017 | 0.016 | 0.021 | 0.090 | nq | Starting HCT3012 |
| 05 | −15° C. | 15 h | 77.3% 20 g | 0.016 | 0.005 | 0.007 | 0.014 | nd | nd | $CH_3CH_2OH$ |
| 06 | −15° C. | 4 h | 64.5% 10 g | 0.011 | 0.003 | 0.007 | 0.016 | nd | nd | IPA |

Notes to table:
[1)]all data listed in the table refer to the isolated wet crystals;
[2)]permanence time at the temperature of choice prior to isolation of wet crystals;
[3)]yields listed in the table refer to the content of HCT3012 in the isolated wet crystals;

SUMMARY TABLE 7[1)]
Crystallization experiments in solvents mixtures

| experiments | Temp. | Time[2)] | Yield[3)] Scale | Naproxen (%) | HCT3013 (%) | NapOMe (%) | HCT3016 (%) | BDMN (%) | BDDN (%) | Notes |
|---|---|---|---|---|---|---|---|---|---|---|
| | | | | 0.052 | 0.017 | 0.016 | 0.021 | 0.090 | nq | Starting HCT3012 |
| 11 | −15° C. | 3 h | 66.8% 3 g | 0.026 | 0.010 | 0.007 | 0.015 | nq | nd | Hexane/ $CH_2Cl_2$/$CH_3OH$ (30 g/3 g/1.5 g) |
| 13 | −15° C. | 15 h | 77.2% 3 g | 0.035 | 0.015 | 0.006 | 0.016 | nq | nq | Hexane/$CH_2Cl_2$ (30 g/3 g) |

Notes to table:
[1)]all data listed in the table refer to the isolated wet crystals;
[2)]permanence time at the temperature of choice prior to isolation of wet crystals;
[3)]yields listed in the table refer to the content of HCT3012 in the isolated wet crystals;

TABLE 8

Crystallization from mixtures of solvents

| Exp. | Temp. | Time | Yield | Naproxen (%) | HCT 3013 (%) | NapOMe (%) | HCT3016 (%) | BDMN (%) | BDDN (%) | Notes |
|---|---|---|---|---|---|---|---|---|---|---|
| | HCT3012 #US07600379 | | | 0.060 | 0.617 | 0.017 | 0.004 | 0.117 | 0.051 | Starting HCT3012 spiked 0.6% 3013 |
| 33 | −10° C. | 15 h | 49.8% | 0.012 | 0.125 | 0.009 | 0.003 | <LOQ | <LOQ | MeOH/acetone |
| 34 | −10° C. | 63 h | 73.6% | 0.022 | 0.180 | 0.012 | 0.003 | <LOQ | <LOQ | IPA/acetone |
| | HCT3012 #US07600379 | | | 0.060 | 0.017 | 0.017 | 0.304 | 0.117 | 0.051 | Starting HCT3012 spiked 0.3% 3016 |
| 35 | 0° C. | 1 h | 79.2% | 0.017 | 0.004 | 0.008 | 0.202 | <LOQ | <LOQ | IPA/THF |

TABLE 9

Crystallization from protic polar solvents (Formamide and Diethyleneglycol).

| Exp. | Temp. | Time | Yield | Naproxen (%) | HCT 3013 (%) | NapOMe (%) | HCT3016 (%) | BDMN (%) | BDDN (%) | Notes |
|---|---|---|---|---|---|---|---|---|---|---|
| | HCT3012 #US07600379 | | | 0.060 | 0.017 | 0.017 | 0.004 | 0.117 | 0.051 | Starting HCT3012 |
| 25 | 2° C. | 15 h | — | 0.012 | 0.011 | 0.015 | 0.003 | <LOQ | <LOQ | HCT 3012: Formamide 1:4 |
| 28 | 3° C. | 15 h | — | 0.019 | 0.006 | 0.012 | 0.004 | <LOQ | <LOQ | Diethyleneglycol ML |

TABLE 10

Crystallization from mixture of solvents.

| Exp. | Temp. | Time[2] | Yield (Scale) | Naproxen (%) | HCT3013 (%) | NapOMe (%) | HCT3016 (%) | BDMN (%) | BDDN (%) | Notes |
|---|---|---|---|---|---|---|---|---|---|---|
| | HCT3012 #US07600379 | | | 0.060 | 0.017 | 0.017 | 0.004 | 0.117 | 0.051 | Starting HCT3012 |
| 26 | −15° C. | 15 h | 48.4% (10 g) | 0.050 | 0.018 | 0.007 | 0.002 | <LOQ | <LOQ | Toluene (20..5 g), n-Hexane(30 g) |
| 37 | −10° C. | 15 h | 17.8% (10 g) | 0.011 | 0.003 | 0.006 | 0.002 | <LOQ | <LOQ | CH$_3$OH/Tol. (15 g/5 g) |
| 38 | 0° C. | 15 h | 66.7% (10 g) | 0.013 | 0.004 | 0.008 | 0.002 | <LOQ | <LOQ | CH$_3$OH/Hexane (15 g/5 g) |
| 45 | 3° C. | 1 h | 48.0% (5 g) | 0.020 | 0.006 | 0.011 | 0.002 | <LOQ | <LOQ | CH$_3$OH/Tol. (9.8 g/0.2 g) |
| 47 | 3° C. | 3 h | 78.9% (5 g) | 0.033 | 0.008 | 0.013 | 0.003 | <LOQ | <LOQ | IPA/Tol. (9.8/0.2 g) |

TABLE 11

Extraction by alcohols (ROH; R = CH$_3$, CH$_2$CH$_3$; HCT 3012/ROH in ½ w/w ratio)

| Exp. | Temp. | Time | Yield | Naproxen (%) | HCT3013 (%) | NapOMe (%) | HCT3016 (%) | BDMN (%) | BDDN (%) | Notes |
|---|---|---|---|---|---|---|---|---|---|---|
| | HCT3012 #US07600379 | | | 0.060 | 0.017 | 0.017 | 0.004 | 0.117 | 0.051 | Starting HCT3012 |
| 24 | 20° C. | 1 h | 45.8% | 0.027 | 0.007 | 0.015 | 0.003 | 0.052 | <LOQ | Lower phase |
| 29 | 3° C. | 3 h | 63.0% | 0.027 | 0.007 | 0.015 | 0.004 | <LOQ | <LOQ | Lower phase |
| 30 | 15° C. | 3 h | 66.3% | 0.029 | 0.007 | 0.012 | 0.003 | <LOQ | <LOQ | Lower phase |
| 31 | 0° C. | 3 h | 69.6% | 0.025 | 0.006 | 0.012 | 0.003 | <LOQ | <LOQ | Lower phase |
| 32 | −5° C. | 3 h | 61.4% | 0.026 | 0.006 | 0.028 | 0.003 | <LOQ | <LOQ | Lower phase |

TABLE 12

Crystallization from CH₃OH (HCT 3012/CH₃OH = ½ w/w)

| Exp. | Temp. | Time | Yield Scale | Naproxen (%) | HCT3013 (%) | NapOMe (%) | HCT3016 (%) | BDMN (%) | BDDN (%) | Notes |
|---|---|---|---|---|---|---|---|---|---|---|
| | HCT3012 #US07600379 | | | 0.060 | 0.017 | 0.017 | 0.004 | 0.117 | 0.051 | Starting HCT3012 |
| 17 | −15° C. | 3 h | 87.5% | 0.021 | 0.008 | 0.013 | 0.003 | <LOQ | <LOQ | |
| 19 | −5° C. | 3 h | 88.0% | 0.021 | 0.008 | 0.012 | 0.003 | <LOQ | <LOQ | |
| 21 | 3° C. | 15 h | 71.9% (10 g) | 0.011 | 0.003 | 0.007 | 0.001 | <LOQ | <LOQ | ML |
| 36 | 3° C. | 15 h | 66.6% (30 g) | 0.006 | 0.002 | 0.005 | 0.002 | <LOQ | <LOQ | Dry powder |
| 40 | −15° C. | 15 h | 71.6% (10 g) | 0.035 | 0.010 | 0.012 | 0.002 | <LOQ | <LOQ | |
| 41 | −15° C. | 15 h | 76.2% (30 g) | 0.028 | 0.008 | 0.014 | 0.002 | <LOQ | <LOQ | |
| 42 | −15° C. to 3° C. | 15 h | 67.7% (30 g) | 0.020 | 0.006 | 0.009 | 0.005 | <LOQ | <LOQ | |
| 43 crist | 3° C. to 5° C. | 15 h | 67.3% (30 g) | 0.011 | 0.003 | 0.007 | 0.005 | <LOQ | <LOQ | |
| | HCT3012 #US07600379 | | | 10.060 | 0.017 | 0.017 | 0.004 | 0.117 | 0.051 | Starting HCT3012 spiked with 10% NAP |
| 50 crist | 3° C. | 15 h | 56.8% (30 g) | 1.014 | 0.003 | 0.006 | 0.002 | <LOQ | <LOQ | |
| | HCT3012 #Ro 2059-20 | | | <LOQ | <LOQ | 0.008 | <LOQ | <LOQ | <LOQ | Starting HCT3012 DSM crist. dry- pure seed |
| 49 | 3° C. | 15 h | 36.3% (30 g) | <LOQ | <LOQ | <LOQ | <LOQ | <LOQ | <LOQ | |
| | HCT3012#US07600379 | | | 1.060 | 0.017 | 0.017 | 0.004 | 0.117 | 0.051 | Starting HCT3012 spiked with 1% NAP |
| 39 | 3° C. | 15 h | 58.4% | 0.134 | 0.003 | 0.008 | 0.002 | <LOQ | <LOQ | |

TABLE 13

Crystallization from methanol (HCT3012/MeOH = 1/10 w/w ratio)

| Exp. | Temp. | Time | Yield Scale | Naproxen (%) | HCT3013 (%) | NapOMe (%) | HCT3016 (%) | BDMN (%) | BDDN (%) | Notes |
|---|---|---|---|---|---|---|---|---|---|---|
| | HCT3012#US07600379 | | | 0.060 | 0.017 | 0.017 | 0.004 | 0.117 | 0.051 | Starting HCT3012 |
| 22 crist | −15° C. | 15 h | 50.6% | 0.068 | 0.015 | 0.016 | 0.004 | 0.067 | <LOQ | |
| | HCT3012 # Ro 2059-20 | | | 0.501 | 0.501 | 0.508 | 0.501 | <LOQ | <LOQ | Starting HCT3012 DSM spiked with 0.5% of all impurities |
| 51 crist | −3° C. | 30 h | 19.0% (30 g) | 0.032 | 0.042 | 0.086 | 0.177 | <LOQ | <LOQ | Spiked with 0.5% of different impurity |
| 52 crist | −3° C. | 15 h | 13.3% (30 g) | 0.036 | 0.053 | 0.102 | 0.218 | <LOQ | <LOQ | Spiked with 0.5% of different impurity |

TABLE 14

Miscellanea

| Exp. | Temp. | Time | Yield Scale | Naproxen (%) | HCT3013 (%) | NapOMe (%) | HCT3016 (%) | BDMN (%) | BDDN (%) | Notes |
|---|---|---|---|---|---|---|---|---|---|---|
| | HCT3012#US07600379 | | | 0.060 | 0.017 | 0.017 | 0.004 | 0.117 | 0.051 | Starting HCT3012 |
| 14 | −13° C. | 18 h | 99.8% | 0.052 | 0.018 | 0.006 | 0.000 | <LOQ | <LOQ | crist. wet- |
| 16 | −15° C. | 2 h | 86.7% | 0.047 | 0.016 | 0.016 | 0.000 | 0.087 | 0.077 | crist. wet |
| 18 | −15° C. | 15 h | — | 0.013 | 0.004 | 0.008 | 0.000 | <LOQ | <LOQ | crist. wet |
| | HCT3012#US07600379 | | | 2.060 | 0.017 | 0.017 | 0.004 | 0.117 | 0.051 | Starting HCT3012 Spiked with 2% of NAP |
| 23 | −40° C. | 15 h | 63.5% | 0.444 | 0.004 | 0.007 | 0.002 | <LOQ | <LOQ | Spiked with 2% of NAP |

The invention claimed is:

1. A method for purifying naproxcinod comprising the steps of:
   a) dissolving or dispersing a mixture containing naproxcinod in a solvent;
   b) cooling the solution or two phases dispersion under stirring to a temperature ranging from −20° C. to 10° C.;
   c) optionally seeding the solution with crystals of naproxcinod;
   d) stirring, by maintaining the temperature in the range from −40° C. to 10° C.;
   e) collecting the formed solid by maintaining the temperature under 15°.

2. The method of claim 1, wherein the mixture contains naproxinod in an amount higher than 90% by weight.

3. The method according to claim 1, wherein the solvent of step a) is a polar protic solvent or an aprotic solvent or a mixture thereof.

4. The method according to claim 3, wherein the polar protic solvent is selected from alcohols, dials, amides or a mixture thereof.

5. The method according to claim 4, wherein the polar protic solvent is methanol, ethanol, isopropanol or 1-butanol, diethylenglycol, or formamide or a mixture thereof.

6. The method according to claim 1, wherein the temperature of step b) is in the range from −15° C. to 5° C.

7. The method according to claim 1, wherein the temperature of step d) is in the range from −15° C. to 5° C.

8. The method according to claim 1, wherein the temperature of step e) is under 10° C.

9. Crystalline naproxcinod obtained by the method according to claim 1.

10. Crystalline naproxcinod having a melting point of about 15° C.

* * * * *